United States Patent
Hobbs et al.

(10) Patent No.: US 10,004,660 B2
(45) Date of Patent: Jun. 26, 2018

(54) METHOD OF THERAPY AND HAPTIC GAMING SYSTEM FOR SENSORY AGNOSIA

(71) Applicants: FLINDERS UNIVERSITY OF SOUTH AUSTRALIA, Bedford Park, S.A. (AU); UNIVERSITY OF SOUTH AUSTRALIA, Mawson Lakes, S.A. (AU); WOMEN'S AND CHILDREN'S HEALTH NETWORK, INC., North Adelaide, S.A. (AU)

(72) Inventors: David Anthony Hobbs, Eden Hills (AU); Susan Loris Hillier, Adelaide (AU); Remo Nunzio Russo, Kensington Park (AU); Alexander William Walker, Henley Beach (AU); Max Bristow Hughes, Kensington (AU); Thomas Samuel Whitby, Glenside (AU)

(73) Assignees: FLINDERS UNIVERSITY OF SOUTH AUSTRALIA, Bedford Park (AU); UNIVERSITY OF SOUTH AUSTRALIA, Mawson Lakes (AU); WOMEN'S AND CHILDREN'S HEALTH NETWORK INC., North Adelaide (AU)

( * ) Notice: Subject to any disclaimer, the term of this patent is extended or adjusted under 35 U.S.C. 154(b) by 411 days.

(21) Appl. No.: 14/646,535

(22) PCT Filed: Nov. 22, 2013

(86) PCT No.: PCT/AU2013/001348
§ 371 (c)(1),
(2) Date: May 21, 2015

(87) PCT Pub. No.: WO2014/078902
PCT Pub. Date: May 30, 2014

(65) Prior Publication Data
US 2015/0290076 A1 Oct. 15, 2015

(30) Foreign Application Priority Data
Nov. 23, 2012 (AU) ............................. 2012905149

(51) Int. Cl.
*A61H 23/00* (2006.01)
*A61H 39/00* (2006.01)
(Continued)

(52) U.S. Cl.
CPC .......... *A61H 23/00* (2013.01); *A61B 5/4827* (2013.01); *A61H 1/0288* (2013.01); *A61H 23/02* (2013.01);
(Continued)

(58) Field of Classification Search
None
See application file for complete search history.

(56) References Cited

U.S. PATENT DOCUMENTS 7,725,175 B2 * 5/2010 Koeneman ............... A61H 1/02
600/546
9,545,356 B2 * 1/2017 Heaton ................ A61H 1/0288

FOREIGN PATENT DOCUMENTS

WO  WO 2005/074371 A2  8/2005
WO  WO 2010/085476 A1  7/2010

OTHER PUBLICATIONS

Official Action for Australia Patent Application No. 2013350319, dated Jan. 20, 2017, 2 pages.
(Continued)

*Primary Examiner* — Stephen R Crow
(74) *Attorney, Agent, or Firm* — Sheridan Ross P.C.

(57) ABSTRACT

A method for treating patients with sensor agnosia is described that uses a gaming system with a specialised two
(Continued)

handed game controller that can provide isolated haptic feedback to the patient's hand that has the greatest sensory agnosia. The controller is designed to be easy to use for patients with limited dexterity and requires the user to use both hands to control the controller. The gaming system provides a range of interactive computer games that provide contextually relevant haptic feedback of varying durations and intensities. Haptic feedback is provided in response to events in a game, and whilst the controller requires two hands, each hand is vibrationally isolated so that haptic feedback is only provided to the desired hand. The system logs usage statistics of the patient and these can be sent back to a clinician for analysis. The system and controller is particularly suitable for children with Cerebral Palsy, but may be used to treat patients with sensory agnosia due to range of conditions.

23 Claims, 16 Drawing Sheets

(51) Int. Cl.
$$\begin{array}{ll}
A63F\ 13/211 & (2014.01) \\
A63F\ 13/24 & (2014.01) \\
A63F\ 13/285 & (2014.01) \\
A61H\ 23/02 & (2006.01) \\
A61H\ 1/02 & (2006.01) \\
A61B\ 5/00 & (2006.01)
\end{array}$$

(52) U.S. Cl.
CPC .......... *A61H 39/007* (2013.01); *A63F 13/211* (2014.09); *A63F 13/24* (2014.09); *A63F 13/285* (2014.09); *A61B 5/4047* (2013.01); *A61B 5/6896* (2013.01); *A61B 5/6897* (2013.01); *A61B 2562/0257* (2013.01); *A61H 2201/0165* (2013.01); *A61H 2201/1635* (2013.01); *A61H 2201/1695* (2013.01); *A61H 2201/5002* (2013.01); *A61H 2201/5005* (2013.01); *A61H 2201/5007* (2013.01); *A61H 2201/5084* (2013.01); *A61H 2205/065* (2013.01); *A61H 2205/067* (2013.01)

(56) References Cited

OTHER PUBLICATIONS

Notice of Acceptance for Australia Patent Application No. 2013350319, dated Apr. 13, 2017, 3 pages.
Official Action for Singapore Patent Application No. 11201504010R, dated Jul. 19, 2017, 3 pages.
Certificate of Grant for Singapore Patent Application No. 11201504010R, dated Sep. 5, 2017, 1 page.
International Search Report prepared by the Australian Patent Office dated Jan. 16, 2014, for International Application No. PCT/AU2013/001348.

* cited by examiner

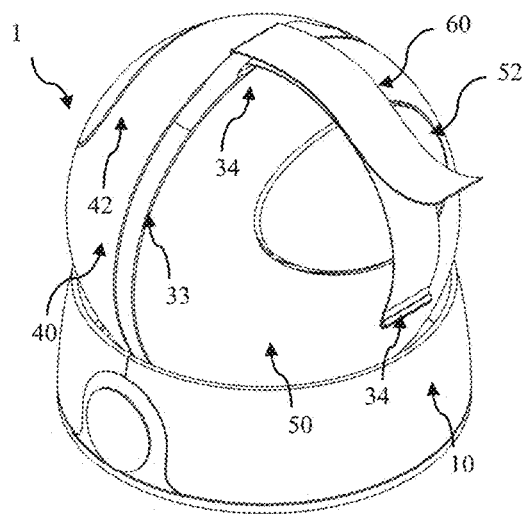
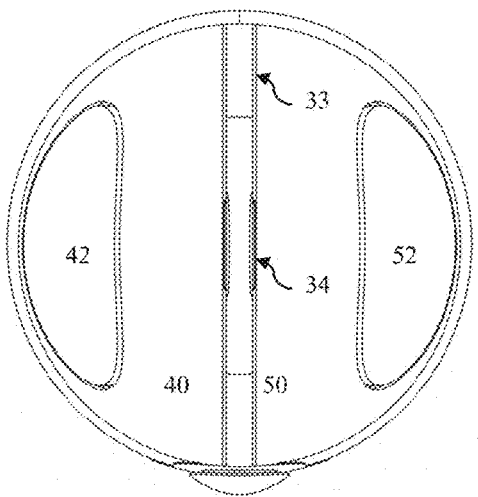
FIG. 4E  FIG. 4F
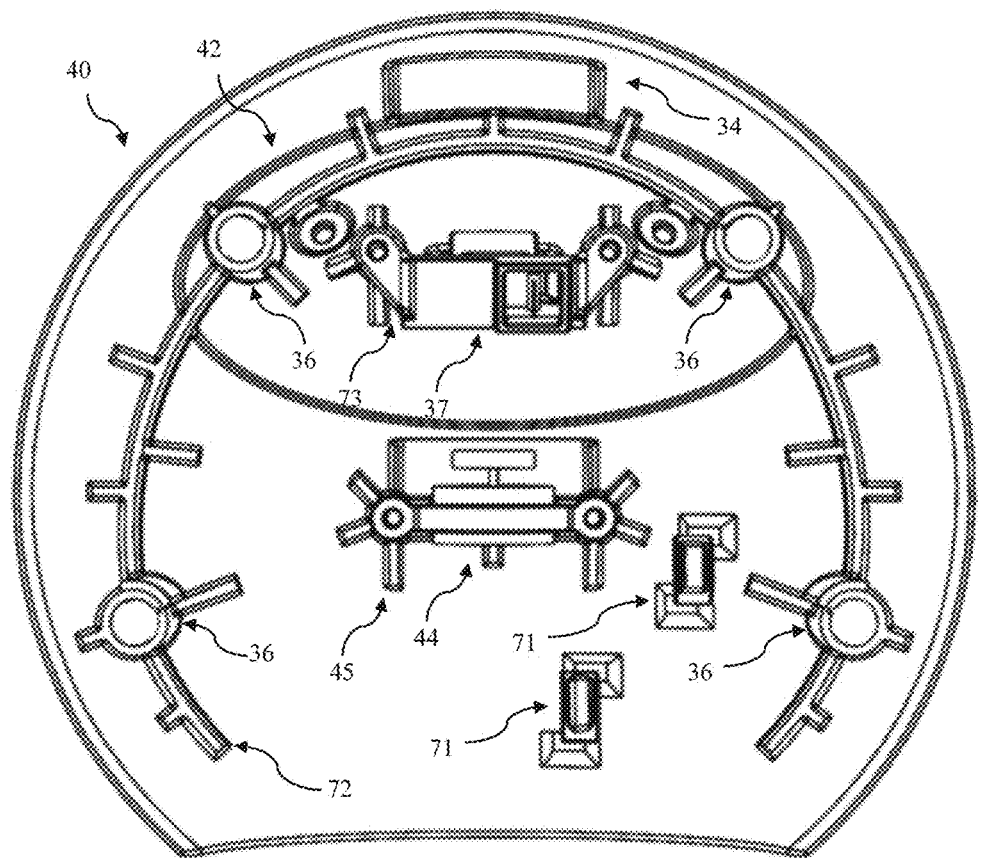
FIG. 5A

METHOD OF THERAPY AND HAPTIC GAMING SYSTEM FOR SENSORY AGNOSIA

CROSS REFERENCE TO RELATED APPLICATIONS

The present application is a national stage application under 35 U.S.C. 371 and claims the benefit of PCT Application No. PCT/AU2013/001348 having an international filing date of 22 Nov. 2013. which designated the United States, which PCT application claims the benefit of Australian Provisional Patent Application No. 2012905149 titled "METHOD OF THERAPY AND HAPTIC GAMING SYSTEM FOR SENSORY AGNOSIA" and filed on 23 Nov. 2012, the contents of each of which are hereby incorporated by reference in their entirety.

TECHNICAL FIELD

The present invention relates to a method of therapy for sensory agnosia and an associated therapeutic input apparatus.

BACKGROUND

Tactile sensory appreciation is required for learning new movement and refining and maintaining the quality of learned movement via complex feed-forward and feed-back systems. Intact sensory function in the hands is essential for the initiation and execution of refined and dextrous hand, grasp, and finger movements. However, many patients suffering or recovering from medical conditions such as cerebral palsy (CP) and stroke, suffer sensory agnosia, which is a lack of touch sensitivity (or a lack of tactile sensory appreciation), often due to the presence of an underlying sensory impairment. This lack of tactile sensory appreciation can lead to neglect of the limb (and subsequent safety issues) and loss of dexterity. Further, this reduced sensory perception is often limited, or at least more severe, in one limb in which case the other limb can become dominant leading to further neglect or 'learned non-use' of the non-dominant limb.

Sensory agnosia often occurs as the result of a stroke, and post-stroke rehabilitation programs have been developed that focus on sensory re-training have proven to be effective (see the systematic review by Schabrun & Hillier, SL 2009, 'Evidence for the retraining of sensation after stroke: a systematic review', Clin Rehabil., vol 23, no. 1, pp. 27-39.). These programs have been based on recent developments in the study of the nervous system which have recognised the capacity of the nervous system to modify its organisation and to re-learn and adapt to new experiences —a process known as neuroplasticity. These post-stroke studies have attempted to re-train sensory function through a long and laborious process of intense and focussed attention that requires the subject to manipulate or touch an object and try to identify sensory attributes while their vision is occluded. This requires dedication and devotion to the task over a number of weeks of intense activity and a desire to persist with a frustrating yet potentially beneficial task.

Despite sensory agnosia (a lack of tactile sensory appreciation) being identified as a clinical issue as far back as 1954 (Tizard, JPM et al. 1954, 'Disturbances of sensation in children with hemiplegia', J Am Med Assoc., vol 155, no. 7, pp. 628-632.), it is only in recent years that more widespread recognition of sensory agnosia in children with CP has occurred. The prevalence of sensory agnosia in patients has been estimated in studies as being between 40% and 97%. However, whilst awareness of sensory agnosia in CP patients has been improving, attempting to influence tactile sensory perception and address the deficit is not, and thus, there is a shortage of therapies for treating CP patients along with knowledge of their effectiveness. As CP is a life-long condition that patients are typically born with, early intervention during childhood is important to yield long lasting benefits, and any therapies developed should ideally be adapted to suit children. In particular, children can be difficult to enthuse and motivate, particularly when gains can be slow, focussed attention is required, and when they don't fully understand or appreciate the benefits that the activity will bring them. Children typically view therapy as 'work' or 'exercise' and are not inherently engaged by the activity. Thus, the methods developed for rehabilitating stroke survivors are not generally applicable to children with CP.

One recent approach to physical therapy (motor rehabilitation) has involved the use of computer games to produce a more engaging and enjoyable method to participate in physical therapy. One approach has been to use off the shelf games and gaming systems that use part or all of a game with limited or no modification. These game and gaming systems typically provide continual visual auditory and occasionally haptic (sensory) feedback, increasing the motivation and desire to play and perform (and thus engaging the patients). Another approach has been to design and develop therapeutic gaming systems from scratch. For example, Flores et al. developed virtual reality video games for stroke rehabilitation of elderly patients (Flores et al., "Improving patient motivation in game development for motor deficit rehabilitation". Proceedings of the International Conference on Advances in Computer Entertainment Technology (2009), Yokohama, Japan: ACM Press).

However, one significant problem with the use of off the shelf games and controllers are that they are designed for use by healthy individuals. As such, the controllers are typically too complex, or require fine motor coordination to use, limiting their use or applicability to people with impaired movement or sensory function. For example, Golomb et al. (Golomb, MR et al. 2011, 'Maintained Hand Function and Forearm Bone Health 14 Months After an In-Home Virtual-Reality Videogame Hand Telerehabilitation Intervention in an Adolescent With Hemiplegic CP', J Child Neurol., vol. 26, no. 3, pp. 389-393) developed a custom virtual reality video game tailored to the needs of a 15-year old boy with hemiplegic CP, observing that ". . . the difficulty with many Wiihabilitation ['Wiihabilitation' refers to using the Nintendo Wii system for rehabilitation therapy] games, which are designed for healthy individuals, may render them inappropriate for use by some disabled children, and may lead to loss of patient motivation" (pp. 392). In particular, children with CP find nimble, dextrous and coordinated finger movement difficult, particularly when speed and control are required, such as is typically found in most commercial off the shelf games. Further, commercial games typically only provide coarse difficulty controls (eg easy/medium/hard) and limited progress information (eg time played, missions completed) limiting the ability of a therapist to customise treatment to an individual or assess the progress of the treatment.

However, custom designed games are not without problems. One problem with custom designed games is that the interface and game play structure have typically been designed to be as closely comparable to physical therapy as possible therefore, motions and activities in the game are of the same repetitive nature as therapies. Thus, whilst such serious games are able to meet (physically based) therapeutic goals to compliment or replace traditional therapy, they suffer from a lack of variation and have failed to provide engaging or entertaining game experiences important in motivating continued use by patients, especially children. Further, these games have typically been used as physical therapies, in which patients are required to perform gross physical movements with arms and/or shoulders, such as stretching, reaching, extending etc, and thus have not been designed to address underlying sensory agnosia.

There is thus a need to provide a therapeutic method for patients with sensory agnosia or at least to provide patients with a useful alternative to current therapies.

SUMMARY

According to a first aspect, there is provided a method for treating a patient, the method comprising:

providing a two-handed controller operable within the patient's known motor capabilities; enabling the patient to engage in an interactive computer game using the two-handed controller; and;

providing haptic feedback to the patient via the two handed game controller as the patient engages with the interactive computer game, wherein the haptic feedback is isolated to one of the patient's hands.

In a further form, the two handed controller comprises a first haptic portion for providing haptic feedback to a first hand, and a second haptic portion for providing haptic feedback to a second hand, and the first haptic portion is isolated from the second haptic portion, and providing haptic feedback to the patient comprises selecting the first haptic portion or the second haptic portion and providing haptic feedback to the selected haptic portion. The choice of which side may be determined based upon the patient's hand with known sensory agnosia. In one form, the first and second haptic portions are located to maximise delivery of haptic feedback to the patient's fingers and palms. In one embodiment a first haptic portion is a first side of the two handed controller and the second haptic portion is a second side of the two handed controller.

In a further form, the two handed game controller provides movement in two axes. In one form, the two handed controller is a pivoting controller and the patient engages in the interactive computing game solely by pivoting the controller using two hands and in an alternative form the two handed controller is a translational controller and the patient engages in the interactive computing game solely by translating the controller in a plane parallel to a base using two hands.

In a further form, the interactive computer game provides a range of contextually relevant haptic feedback of varying durations and intensities. In one form, the step of logging the haptic feedback provided to a patient engaging in the interactive computer game. In one form, events in the interactive computer game are assigned a relative feedback strength normalised to a reference feedback intensity and duration s. In one form, logging the haptic feedback comprising logging the duration and strength of each haptic feedback event. In one form, the method further comprises logging usage one or more usage metrics of the patient engaging in the interactive computer game, wherein the one or more usage metrics are selected from the group comprising time, day, duration of session, and controller position.

In a further form, the step of enabling the patient to engage in an interactive computer game further comprises detecting when both hands of the patient are in contract with the controller, and only allowing the patient to interact with the game when both hands are detected as being in contact with the controller.

In a further form, the step of enabling the patient to engage in an interactive computer game further comprises providing at least one interactive computer game comprising one or more levels, and the one or more levels comprise procedurally generated content to provide repeated game play. In one form, the game comprises procedurally generated content. In a further form, the games are designed with a gentle complexity ramp. In one form, the gentle complexity ramp comprises a plurality of optional challenges in a level, wherein each of the optional challenges being increasingly difficult to achieve. In a further form, the interactive computer games comprise high quality graphics and sounds to provide entertainment value to the patient in addition to therapy.

In a further form, the patient is diagnosed with Cerebral Palsy.

According to a second aspect, there is provided an input apparatus comprising:

a base;

a top section;

a mount for mounting the top section relative to the base, wherein the mount allows the top section to move in two axes relative to the base to define the input provided by the device;

a communications interface;

a first surface on a first side of the top section, for a first hand of the user;

a second surface on a second side of the top section, for a second hand of the user; and at least one haptic actuator to provide haptic feedback to the first surface or the second surface, wherein the first surface and the second surface are substantially isolated such that the haptic feedback can be provided independently to the first or second surfaces.

In a further form, the input apparatus further comprises a controller for receiving a haptic selection command via the communications interface and enabling haptic feedback to be provided to the first surface or the second surface based upon the haptic selection command. In a further form, the at least one haptic actuator further comprises a first haptic actuator to provide haptic feedback to the first surface, and a second haptic actuator to provide haptic feedback to the second surface, and the first surface is isolated from the second surface. In one form, the first haptic actuator is mounted in a haptic module mount located in the first side and the first side is mounted to a central plate via a plurality of isolation mounts, and the second haptic actuator is mounted in a haptic module mount located in the second side and the second side is mounted to the central plate via a plurality of isolation mounts. In one form, the isolation mounts are rubber mounts.

In a further form, the input apparatus further comprises at least one strap for strapping a hand to either the first or the second surface. In one form, the at least one strap is a removable strap.

In a further form, the mount is configured to self-centre the top section over the base.

In a further form, the input apparatus further comprises a first proximity detector for detecting if a hand is placed on the first surface, and a second proximity detector for detecting if a hand is placed on the second surface.

In a further form, the first surface and the second surface are located to maximise delivery of haptic feedback to the patient's fingers and palms.

In a further form, the first and second sides are concave and are arranged relative to each other such that in use a user is required to contact both the first and second surfaces to pivot the controller.

In a further form, the input apparatus further comprises a single button located on a position other than the first surface or the second surface.

In a further form, the mount is a translational mount allowing the top section to move within a plane parallel to the base defined by an X axis and a Y axis, and the translation mount is configured to measure the X and Y positions within the plane.

In a further form, the input apparatus further comprises a first linear potentiometer for reporting a X position within the plane and a second a second linear potentiometer for reporting a Y position within the plane.

In a further form, the mount is a pivoting mount allowing the top section to pivot relative to the base, and detects the zenith and azimuthal angle of the top section relative to an axis normal to a plane parallel to the base.

In a further form, the input apparatus further comprises a position detection circuit comprising a first potentiometer for detecting the zenith angle, a second potentiometer for detecting an azimuthal angle, wherein the position detection circuit is configured to project the detected zenith angle and azimuthal angle to a (X,Y) position within the plane.

According to a third aspect, there is provided a treatment system comprising:

an input apparatus comprising a first surface and a second surface according to the second aspect;

a display device;

a processor; and a memory, wherein the memory comprises instructions to cause the processor to execute an interactive computer game wherein the interactive computer game provides haptic feedback to the patient from the computer game via the input apparatus, wherein the haptic feedback is isolated to one of the first surface or the second surface.

According to a fourth aspect there is provided a non-transitory computer readable medium comprising instructions for causing a processor to execute an interactive computer game, wherein the instructions further comprises instructions for generating haptic feedback to one of the first surface or the second surface in an input apparatus of the third aspect.

In a further aspect, the computer readable medium comprising instructions for implementing the method of the first aspect (and further forms).

BRIEF DESCRIPTION OF DRAWINGS

Embodiments of the present invention will be discussed with reference to the accompanying drawings wherein:

FIG. 4E is an isometric view of a controller according to another embodiment, and FIG. 4F is a side view of the controller illustrated in FIG. 4E;

FIG. 5A is an internal side view of a first side of the controller illustrated in FIGS. 4A to 4D.

In the following description, like reference characters designate like or corresponding parts throughout the figures.

DESCRIPTION OF EMBODIMENTS

Figure 1:
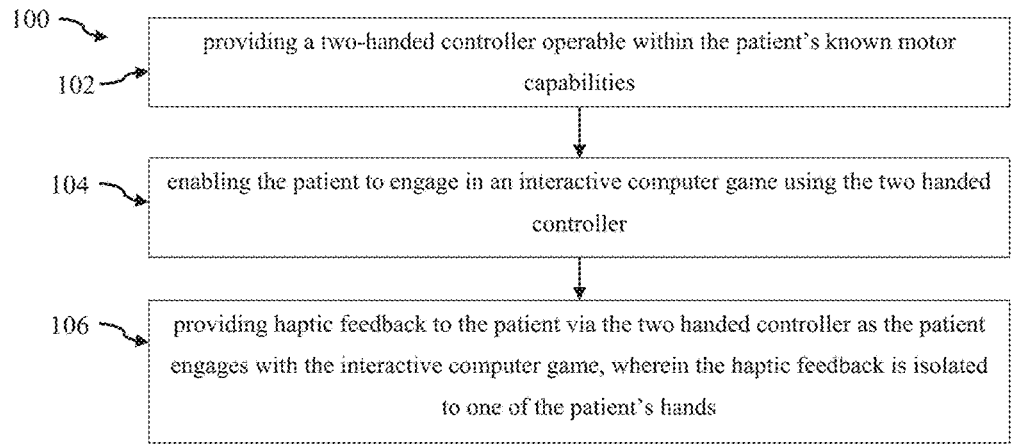
FIG. 1 is a flowchart of a method of treatment according to an embodiment.

Embodiments of a method of treatment for patients with sensory agnosia (a lack of tactile sensory appreciation) will now be described. FIG. 1 illustrates a flowchart 100 of a method of treatment according to an embodiment. Step 102 comprises providing a two-handed controller operable within the patient's known motor capabilities; step 104 comprises enabling the patient to engage in an interactive computer game using the two handed controller; and step 106 comprises providing haptic feedback to the patient via the two handed controller (as the patient engages with the interactive computer game, wherein the haptic feedback is isolated to one of the patient's hands). Specifically, haptic feedback is isolated so that it is provided either solely or at least substantially to the hand with the greatest sensory agnosia. That is, if a patient suffers sensory agnosia mostly in the left hand, then haptic feedback (eg vibrations) can be provided just to the left side, and the right side of the controller doesn't vibrate. Alternatively, if the patient suffers sensory agnosia mostly in the right hand, then haptic feedback (eg vibrations) can be provided just to the right side, and the left side of the controller doesn't vibrate. Haptic feedback can be selectively provided to a first haptic portion of the controller or to a second haptic portion of the controller. The haptic portions and/or haptic delivery mechanisms are isolated from each other to prevent transfer of vibrations or other haptic feedback. The first haptic portion may be the entire first side of the controller and the second haptic portion may be the entire second side of the controller, and the two sides may be vibrationally isolated from each other. Alternatively, the first haptic portion may be a first surface on the first side of the controller and the second haptic portion may be a second surface on the second side of the controller, and the first surface may be isolated from the first side, and the second surface may be isolated from the second side, in which case the first and second sides may not joined or part of the same structure.

Selective or isolated haptic feedback is provided to prevent or substantially reduce the effects of sensory extinction which can occur if haptic feedback is provided equally to both hands. Sensory extinction is a medical phenomenon which is defined as the failure to report sensory stimuli from one region if another region is stimulated simultaneously, even though when the region in question is stimulated by itself, the stimulus is correctly reported. Sensory extinction is particularly undesirable from a therapeutic benefit perspective, as if haptic feedback was provided to both hands, then the brain will likely ignore the weak sensory stimuli from the hand affected by sensory agnosia in preference for the stronger stimuli from the unaffected or less affected hand, thereby negating or reducing any therapeutic benefit of the haptic feedback for sensory agnosia. Providing sensory feedback to the most affected hand has the potential to retrain and improve touch sensitivity in the affected hand and thus reduce sensory agnosia (ie improve the sense of touch in the affected hand).

An input apparatus (or input device) embodied as a two handed controller and associated serious games have been developed which provide contextually relevant selective haptic feedback to an affected hand. Providing repeated contextually relevant afferent stimulation or feedback only to the affected limb whilst in the context of a game with associated goals, audio cues and visual cues, increases the likelihood that, over time, neural pathways for signals from the affected hand will be strengthened and reinforced (ie neuroplastic learning). This trained reinforcement combats limb neglect and has the potential to improve the sense of touch and thus provide an ongoing therapeutic benefit to the patient.

Embodiments of the method of treatment use a serious game approach, but unlike most prior art serious game methods which attempt to mimic or provide physical therapy to target motor capabilities, the present embodiments have been designed to utilise an interactive haptic computer gaming system to influence sensory function of the patients and train/re-train the impaired sense. In particular, embodiments of the system only require minimal movement rather than the large scale gross range of movement used in physical therapy games. This method of treatment using serious games is particularly suitable for use with children diagnosed with Cerebral Palsy (CP). As such, in the discussion that follows. patients will typically be referred to as CP patients. However, it is to be understood that the method is for treating sensory agnosia irrespective of the underlying cause (eg CP, stroke, trauma, etc). Further, in this context, a game comprises an interactive environment in which patients are provided with a visual scene using a graphic display device, and the patient uses an input apparatus such as a two handed controller to control an element in the game (eg a plane, car or spaceship). The player receives rewards for performing tasks or reaching a goal, and receives haptic feedback as they attempt to complete tasks or reach a goal. An interactive game shares similarity with a rehabilitation training program or rehabilitation exercises, in that a patient may repeat a series of moves/controls/actions, however a game typically differs due to either the intrinsic variability or randomness that can be included in a game environment and/or the task or goal orientated nature of the interactive gaming environment. That is, games tend to be more varied to encourage repeated game play. However, it should be noted that embodiments of the game controller (or input apparatus) described herein could be used in a training program or a set of repeated exercises in which haptic feedback is selectively provided to one hand or the other. Also, it is noted that in some embodiments the controller may be able to provide either no haptic feedback (ie it may be switched off) or haptic feedback may be provided to both hands simultaneously, for example when being used by a user without sensory agnosia.

Referring back to FIG. 1, step 102 comprises providing a two-handed game controller operable within the patient's known motor capabilities and step 104 comprises enabling the patient to engage in an interactive computer game using the two handed controller. That is, the patient must have sufficient motor capabilities to use (ie push, pull, move or tilt) the controller in the context of the interactive computer game. Note that the user does not necessarily have be able to hold the controller or have sufficient motor control to ensure that a hand remains on the controller as in such cases straps can be provided on the controller to assist an affected hand (or hands) to remain on the controller during the game. All that is required is sufficient motor control to allow the user to move (ie push/pull or tilt) the controller.

The two handed controller is used to provide movement in two axes. The controller may allow translational movement in an X-Y plane parallel to the base of the controller, or a pivoting controller (eg analogue stick) which allows angular movement (zenith, azimuth). The angular movement can be projected (transformed or mapped) onto a position in the X-Y plane parallel to the base if desired. The patient engages in the interactive computing game solely by translating or pivoting the controller using two hands and thus this two dimensional input can be used to control an object in a game. By restricting the control to joystick only movements, only gross hand/arm movements are required to play the games, and no button presses are required. This ensures that the games have an easier 'entry level', meaning that children with CP can succeed within the game, which is an important aspect with respect to 'buy in', with game complexity and the degree of difficulty steadily but not quickly programmed into the game play. In other words, the 'complexity ramp' is gentle and not rushed. The combination of easier game play and simpler control mechanics (eg up down left or right movements only) than conventional off the shelf games leads to a more accessible gaming system for children with CP (or other patients with sensory agnosia). A single input button can be used to pause the game and access other menus (eg re-start, stop, game selection etc). Further buttons can also be provided if desired. In use, haptic feedback can be separately or selectively provided to each hand (or the surface or side each hand will touch). The choice of which hand (or side) haptic feedback is directed is determined based upon the patient's hand with known sensory agnosia. This selection is determined prior to use, and can be locked or password controlled to prevent unauthorised changes. In one aspect the gaming system could store the appropriate side for a user and the gaming system will select or instruct the controller of the appropriate side to use once a user signs into the system. In one embodiment each user has a stored user profile which may include the haptic mode (first side/second side/both side/off). The haptic mode for a user could be configured by an administrator (eg a clinician or parent) or optionally by the user using an administration module of the software. The user profile may also include usage data and usage metrics which can be provided or sent to a clinician. In another embodiment a switch could be provided in the base of the controller to allow selection of haptic portion that haptic feedback is to be provided. A lockout mechanism could be provided as well by only enabling the switch and storing of the haptic mode of the switch when an authorised user is logged into the system, or a command is sent by the software to read the current state of the switch and set the haptic mode (ie combined hardware/software control of the haptic mode). Alternatively, a series of specific inputs (eg button presses and/or orientation changes of the controller) are required before the switch state is read and used to set the haptic mode of the controller.

Figure 12:
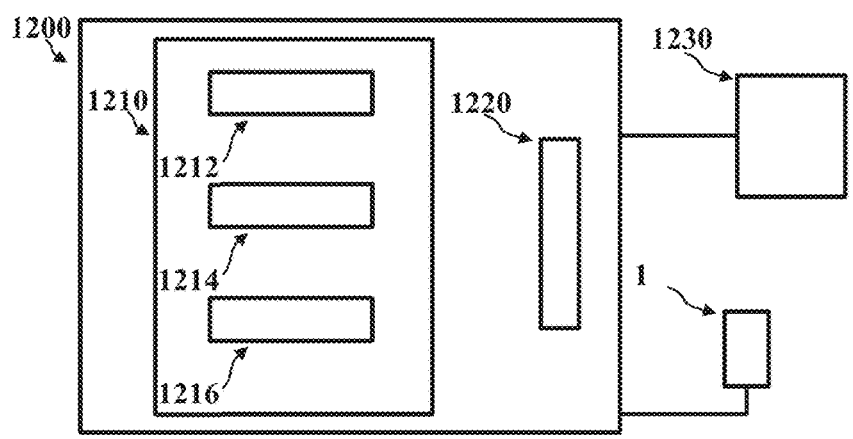
FIG. 12 is a block diagram of a computing system according to an embodiment.

The serious game treatment system can comprise a display device, a processor and a memory and an input apparatus (or input device) as described herein. The memory may comprise instructions to cause the processor to execute an interactive computer game wherein the interactive computer game provides haptic feedback to the patient from the computer game via the input apparatus, wherein the haptic feedback is isolated to one of the patient's hands. The processor memory and display device may be included in a standard computing device, such as a desktop computer, a portable computing device (or apparatus) such as a laptop computer, tablet or smartphone, or they may be included in a customised device or system (eg like a games console). The computing device may be a unitary computing or programmable device, or a distributed device comprising several components operatively (or functionally) connected via wired or wireless connections. The computing device 1200 as illustrated in FIG. 12 comprising a central processing unit (CPU) 1210, a memory 1220, a display apparatus 1230, and at least one input apparatus 1 such as embodiments of a two handed controller described below. Other input devices (eg keyboard, mice, etc) may also be included. The CPU 1210 may comprise an Input/Output Interface 1212, an Arithmetic and Logic Unit (ALU) 1214 and a Control Unit and Program Counter element 1216 which is in communication with input and output devices (eg input apparatus 1 and display apparatus 1230) through the Input/Output Interface. The Input/Output Interface may comprise a network interface and/or communications module for communicating with an equivalent communications module in a user input glove using a predefined wired or wireless communications protocol (e.g. Bluetooth, Zigbee, IEEE 802.15, IEEE 802.11, TCP/IP, UDP, etc). The two handed controller (input apparatus) may communicate with the computing device using a wired connection or a wireless connection and may provide positional information or input signals to the computer (ie joystick position or orientation). The two handed controller may allow direct control of the haptic actuators in the controller by the computer, or the controller may receive haptic feedback signals from the computing device that are used to control the amount and intensity of haptic feedback delivered by a haptic actuator. A wired connection may be used to provide power to the two handed controller, or the two handed controller may include a battery (including a rechargeable battery). A graphical processing unit (GPU) may also be included. The display apparatus may comprise a flat screen display (eg LCD, LED, plasma, touch screen, etc), a projector, CRT, etc. The computing device may comprise a single CPU (core) or multiple CPU's (multiple core). The computing device may use a parallel processor, a vector processor, or be a distributed device. The memory is operatively coupled to the processor(s) and may comprise RAM and ROM components, and may be provided within or external to the device. The memory may be used to store the operating system and additional software modules that can be loaded and executed by the processor(s). The memory may run software or execute instructions to enable an interactive game through the use of a display device and an input apparatus 1 which is used to provide selective isolated haptic feedback to a user. Embodiments of input apparatuses are described below.

Embodiments of a serious gaming system which comprises a series of haptically-enabled serious games will now be described. The games are being developed with an emphasis on tactile sensory feedback and "cognitive engagement" to encourage long term play, motivation and compliance, and despite being therapeutic in nature, were designed to be played as though they were simply games. In order to provide a therapeutic effect, each of the games provides a range of contextually relevant haptic feedback of varying durations and intensities. That is, the games have frequent and pronounced use of vibration, isolated to an affected hand, that is contextually relevant to events within the game. The games have been designed to feature high quality graphics, as well as interesting and varied game play so as to provide entertainment as well as therapy, thereby increasing "buy-in" by patients. That is, the look and feel of the game (ie form) is more similar to existing commercial gaming systems, whilst retaining the functionality of a therapeutic serious game.

Further, the system can be configured to log the haptic feedback provided to a patient engaging in the interactive computer game. The system can log the vibration 'dosage', including the duration and strength of each vibration, at both an individual (single game) and cumulative level (multiple games). In addition to vibration dosage, other metrics of interest can be logged. This includes the joystick motion over time or controller position, duration of play sessions, general aptitude at the game, time spent in the menu system and time spent inactive during play. Additionally the system can include a detector to detect if both hands of the patient are on the controller.

Figure 13:
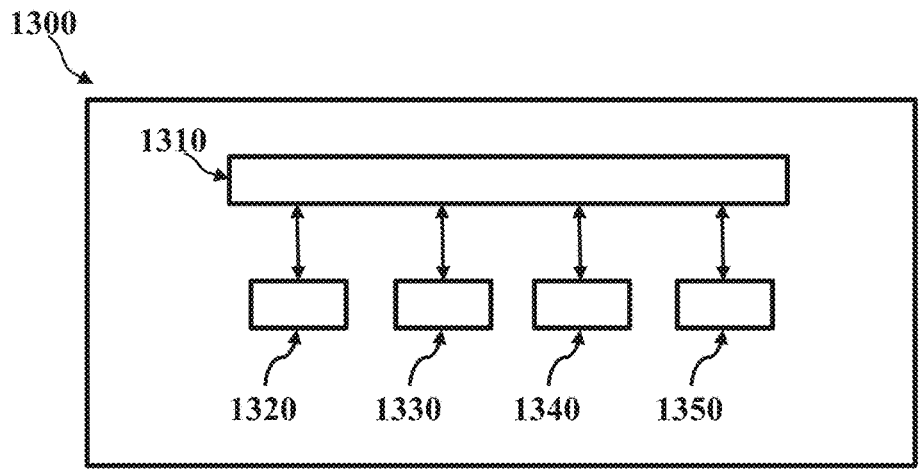
FIG. 13 is a functional block diagram of the operational software for executing an interactive game according to an embodiment.

FIG. 13 is a functional block diagram of the operational software module 1300 for executing an interactive game according to an embodiment. The operational software module comprises a control module 1310, an administration module 1320, a logging module 1330, an I/O and communications module 1340 and a games library (or catalogue) 1350. The control module 1310 controls the overall program flow, allocation of resources, configuration of games and user profiles, loading of other modules to enable the use of the system, etc. In one embodiment the control module executes a session manager module.

Figure 14:
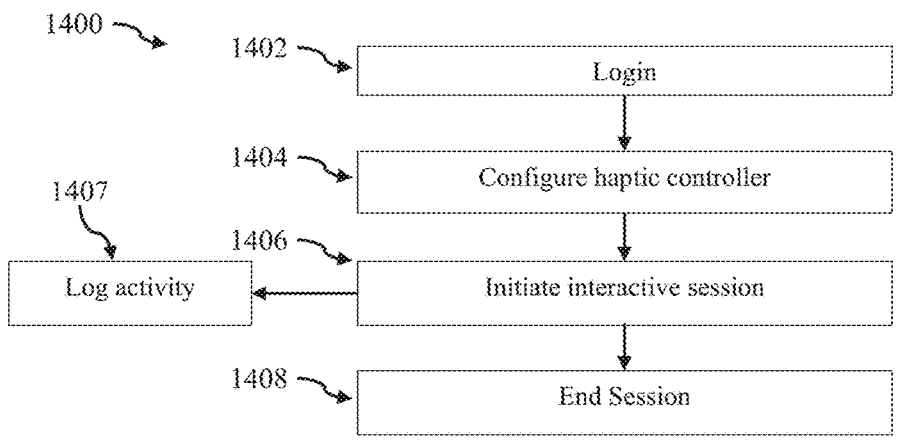
FIG. 14 is a flow chart of the session manager according to an embodiment.

FIG. 14 is a flow chart 1400 of the session manager module according to an embodiment. At step 1402 a login is provided to allow a user to login. This may be an authenticated login with a username and password, or simply require the entering in of a username, or selecting a predefined user or guest account in a user interface. Once a user is logged in, at step 1404 the haptic controller is configured based upon the haptic mode stored in the user profile. In one embodiment this comprises the I/O and communications module 1340 sending a haptic configuration command to the two handed controller to select which haptic portion or which haptic actuator is to be used in response to receiving a haptic feedback signal. In another embodiment the I/O and communications module 1340 sends or provides the haptic mode to a game module wherein the game module sends haptic feedback to the selected haptic portion or haptic actuator in the game controller (ie the game sends directed feedback signals based upon the provided haptic mode). Once the haptic controller is configured, the control module initiates an interactive session 1406. During the interactive session the user may be provided with a catalogue or menu of games in the games library 1350 that may be selected and played, along with a demo of each game, and any usage statistics or metrics obtained from one or more user profiles such as high scores, or previous achievements. A user may select and play one or more games and once they have finished they may end their session at step 1408.

Whilst the user is engaged in the interactive session, the logging module 1330 logs the activity of the user in step 1407. Activity logged may comprise time spent in the session, time spent in games, as well as the amount and intensity of haptic feedback provided to the user during a game. At the end of the session the logging data can optionally be transmitted to a clinician or other user for analysis and review. The logging module 1330 may also perform aggregation and analysis of the data to calculate usage metrics for subsequent reporting.

The control module and/or the gaming library 1350 may also implement an incentives module to encourage and increase system usage. The incentives module may be used to limit a user from playing one or more games in the gaming library until certain requirements are met. That is, certain features may be locked until the user has met the unlocking criteria, such as total time spent playing games, or reaching a certain achievement or score in a game.

Figure 15:
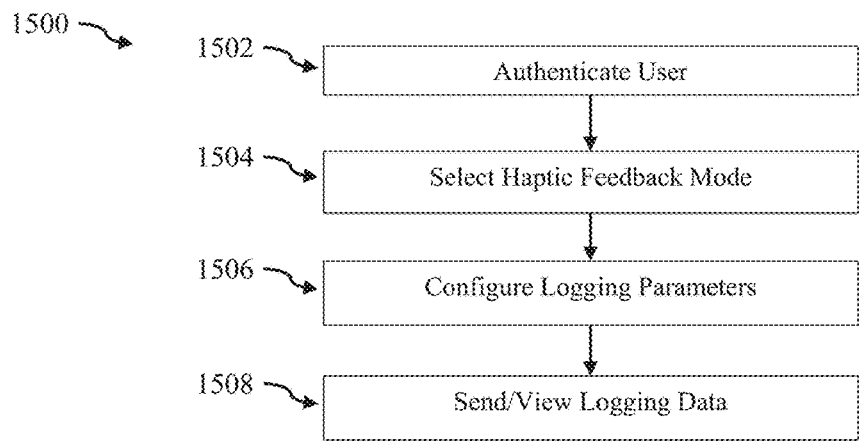
FIG. 15 is a flow chart of the administration module according to an embodiment.

FIG. 15 is a flow chart 1500 of the administration module 1320 according to an embodiment. At step 1502 a user is authenticated to determine if they have sufficient privileges to execute or access the administration module. If the user is authenticated, the user at step 1504 may then select the haptic feedback mode for one or more users of the system. Similarly, at step 1506 the user may configure one or more logging parameters for one or more users. Logging parameters comprise the type and amount of information to be logged, such as haptic feedback, time spent in various modes (in game, browsing games, etc), time of day along with the granularity of data, and whether summary statistics, data aggregation or other data analysis is to be performed on raw or stored logged data. For example, the system may log every haptic event, the intensity and duration, and/or only the total for each session. In step 1508 the authenticated user may initiate sending of the logging data to another user such as a remote clinician or they may configure when data is to be sent or alternatively they may view the logged data. The administration module 1320 may also allow remote access via the I/O and communications module 1340 by a remote user such as a clinician. This would allow the clinician to review treatment, download data or configure the feedback to be provided by a game. For example, the clinician could choose a target amount of haptic feedback to be provided to a user, and the target amount could be used by a game in the game library to determine how often to provide haptic feedback or the intensity. As the games may use procedurally generated levels, in which case haptic feedback events or triggers may be pseudo-random rather than controlled, this may be implemented by a setting on a normalised scale. For example, the scale may range from 0 to 10 where 0 is no feedback and 10 is maximum feedback. This feedback setting can be used by the game to control when and/or how much haptic feedback is delivered in response to a haptic feedback event (or trigger) in a game. The administration module may also allow an authenticated user to configure the incentive module, such as the conditions under which new games will be unlocked.

Figure 16:
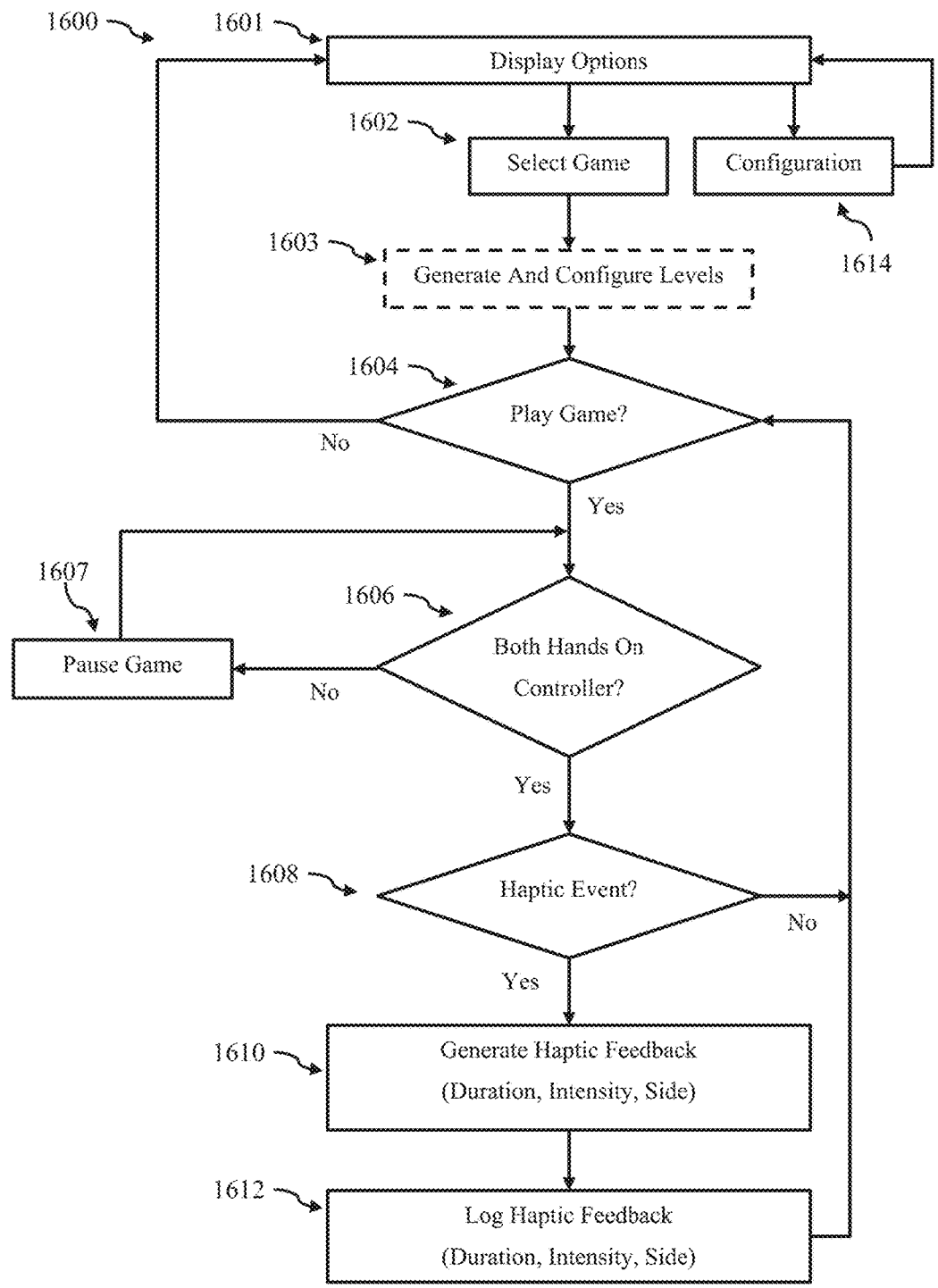
FIG. 16 is a flow chart of an interactive computer game session according to an embodiment.

FIG. 16 is a flow chart 1600 of an interactive computer game session (eg blocks 1406 and 1407 of FIG. 14) according to an embodiment. Once the interaction session begins, the available options are displayed to a user 1601. This may be a home screen showing a set of icons representing each of the games in the game library 1350, along with a window showing a demo of one of the games and other metadata (high scores, achievements, time played, etc), and other icons or input buttons as to allow the user to end the session 1408, or performing configuration of the system. Selecting a configuration option 1614 executes the administration module 1320 which in one embodiment including executing the flowchart shown in FIG. 15 to allow a user to configure which side the haptic feedback is to be delivered to a user by the controller. The user may select a game 1602, which optionally triggers the game to generate and configure levels 1603 in the case of a procedurally generated game as discussed below. The user can then begin to play the game 1604 until such time as they wish to stop playing or the game ends, at which point control is returned to the home screen (ie display options point 1601). At the control screen they can then select another game to play. In an alternative embodiment, the player may be forced to login each time they wish to play a game. Thus login step 1402 and configuration of the haptic controller 1404 could be performed as part of step 1602 and after step 1406, ie after initiation of an interactive session.

Whilst the user is playing the game, the system checks that both hands of the user are on the controller 1606. If both hands are not detected as being on the controller or at least in close proximity to the controller then game play is paused 1607 until the users hands are placed back on the controller. Whether the users hands are on the controller will typically be determined by proximity sensors on the controller, and strictly these may only be able to detect that a hand is within a predefined range of the sensor (ie the range of the sensors) which is interpreted as being on the controller (ie the hands are sufficiently proximal to the controller to allow game play, or within a proximity limit to allow game play). Checking may be continuous or periodic or may be implemented by the sensor or two handed controller generating an interrupt to the game software if both hands are not detected as being on the controller. If both hands are on the controller then game play continues until a haptic event is generated 1608. This may be due to a user hitting an obstacle, collecting a token or reward, or completing a task. Once a haptic event is triggered, then appropriate haptic feedback is generated 1610. This may include determining the duration and intensity of the haptic feedback for example to determine the signal parameters provided to the haptic actuator, as well as which side (or which haptic actuator) the feedback is to be generated in. The haptic feedback parameters or a haptic feedback signal is then sent to the control board 14 of the controller via the I/O and communications module 1340. Configuration and generation of the signal to the haptic actuator may be performed by one or both of the control software on the computing device and the control board 14 in the controller. Once the haptic feedback is generated, the haptic feedback is logged 1612 by the logging module 1330. Game play then continues 1604. For the sake of clarity, game play continues whilst there are no haptic events (ie the No branch of 1608). Note that generation and logging of haptic feedback could be performed in parallel with game play (eg as a separate thread), and logging may be performed immediately after the event, or the logging events could be stored in a queue which is periodically written to file at a convenient time.

To maintain accessibility in a game where the player is given freedom of movement, several guiding features can be implemented to both passively and actively direct the player to move in the right direction. For example, force feedback can be used to keep players on the right path in a game or the object of control in a video game may be locked onto a specific path. The level of guidance provided can be controlled (eg via a configuration menu) so that the users face an appropriate difficulty level.

In some embodiments, the games are designed to promote repeated gameplay and increase or maintain the entertainment value. In some embodiments, this can be achieved through providing multiple paths through a level or multiple solutions to playing the games, so more difficult options yield higher rewards but require practice to attain. Additionally or alternatively, some embodiments of the games use procedurally generated content to make each game played unique and improve their replay value. The layout of levels, goals or obstacles can be designed according to a combination of random generation and specified constraints, rather than by deliberate design. The level design for most games uses a limited interaction model that is relatively simple and can be efficiently implemented using procedurally generated levels. Procedurally generated levels allow for each play session to have different challenges based on the same underlying rules, improving longevity of the product. The amount of work is minimised in terms of tailoring level design and asset creation that would otherwise be necessary for a fully designed level and providing the algorithm is sufficiently detailed, the level design will be varied but still be possible to successfully complete.

Although procedural generation does have positive effects in lengthening a game's lifespan, it poses problems in measuring a player's progress. With strictly designed levels, data between participants is perfectly comparable; however levels developed randomly create a unique experience between players that is not directly comparable. This problem can have several solutions. Changing the way data is tracked through the game; rather than storing absolute information over the entire scope of the game addresses this issue. The game can record the player's ability to meet and solve various atomic challenges, (such as clearing a specific obstacle or collecting a specific item within the game), keep measure of the player's starting distance from the object and measuring other factors such as the time taken to get it, or the path taken to avoid it. This breaks the games down into more manageable units that can be compared to determine improvements in performance. The seed used in generating each level can also be recorded or specified. This ensures the levels follow the constraints of the algorithm but remain the same so long as the same seed is used.

Another method of providing appropriate difficulty and repeat gameplay is to introduce variation into gameplay. Rather than simply increasing the number of challenges, the game can present various goals or obstacles in the game that are not fundamentally necessary for the game to continue or even complete, but the achievement of these optional goals will increase the player's overall score. Instead of accelerating difficulty through time constraints and increased challenges, each level can provide one or more optional challenges that are increasingly difficult to achieve. They demand faster or more precise movements from the player, or forethought and planning. A player's score in each individual level remains a good measure of their ability within the game, but the flexible manner in which that score can be achieved allows players of all levels of ability to attempt the same level and experience different levels of difficulty. Difficulty can also be provided through the method with which players interact with the game. For example, changing the perspective of the camera changes the way the player must interact with the game without changing the core logic of the game or causing disorientation. For example, in Biplane 1922, a biplane flight simulator, changing the camera from an overhead perspective to a side profile perspective means the player no longer controls their horizontal position, but they must instead manage their altitude. This does not alter the way the game is played substantially, but instead changes the nature of the challenges presented, requiring an adjustment to their control within the game world.

Figure 11A:
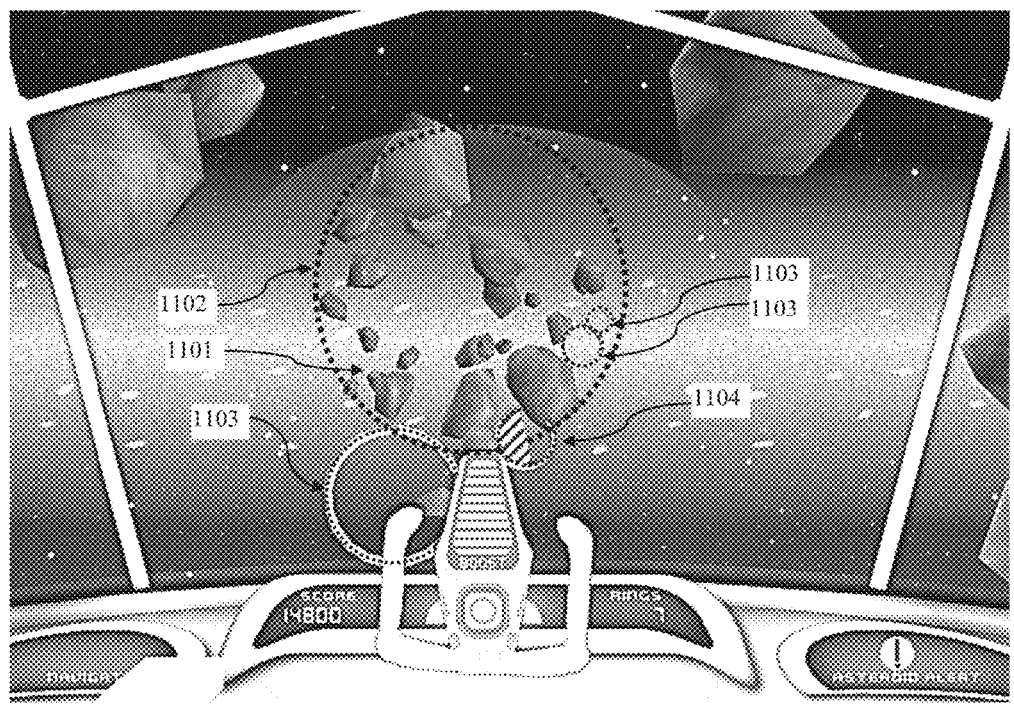
FIG. 11A is a screenshot of a therapeutic game according to an embodiment.

One game developed is called Space Stuntz, and is a first person space flight game in which the player controls a space ship with the primary goal of flying through as many coloured rings as possible. Each level in the game comprises a linear sequence of rings that are generated with a fixed distance from one to the next and a random amount of off-centre variation. Rings may appear in a straight line or they may require the player to move sideways or up and down to reach them. As the game's difficulty increases, both the distance from one to the next and the maximum possible off-centre variation increases, meaning rings appear further and further apart and the player must travel farther along each axis to reach them. The game introduces challenge and variation in several ways. Periodically, asteroid fields will appear in which variable sized asteroids move towards the player, with speed and quantity depending on the level the player has reached. Colliding with asteroids will deplete the player's shield. There are also special rings in the game that can affect decisions the player makes. Infrequent appearing "booster rings" will double the player's speed and craft responsiveness for a short time, but doubles all points earned as long as the boost is effective. Special bonus rings also appear in the game that replenish shields and have a large score bonus, but these do not appear on the same linear path as the other rings, meaning they are difficult to pass through without missing other rings in the sequence. Both booster and bonus rings are entirely optional, so the player can decide if the risk is worth the reward, based on their current position in game as well as their confidence or skill. This offers ways for more advanced players to achieve more difficult goals, to earn more points. FIG. 11A illustrates an annotated screen shot from the game Space Stuntz. The screen shows a cockpit view of space showing an asteroid field comprising asteroids (dark shapes) of varying sizes and shapes generally within dotted circle 1102 and rings 1103, including special ring 1104 (annotated with dotted lines).

Haptic feedback is used extensively in Space Stuntz. All feedback runs for a duration with a normalized strength s. Weak vibrations (s=0.15) lasting no more than half a second are used for events such as passing through rings or completing levels. Larger vibrations (s=1.0) are used when the craft collides with objects such as rings or asteroids. In addition to this, constant vibrations are used during asteroid storms and boosts, to indicate changes in the environmental conditions to the player; these are of relatively low intensity (s=0.3). The game meets accessibility requirements as only the joystick is needed to manoeuvre the craft and no buttons are necessary to play. As the course is theoretically infinite and level design is procedural, a custom data logger program keeps track of relative values between the spaceship and the next ring in the sequence, which can be used to determine how effectively players move in different directions over a broad data set.

Figure 11B:
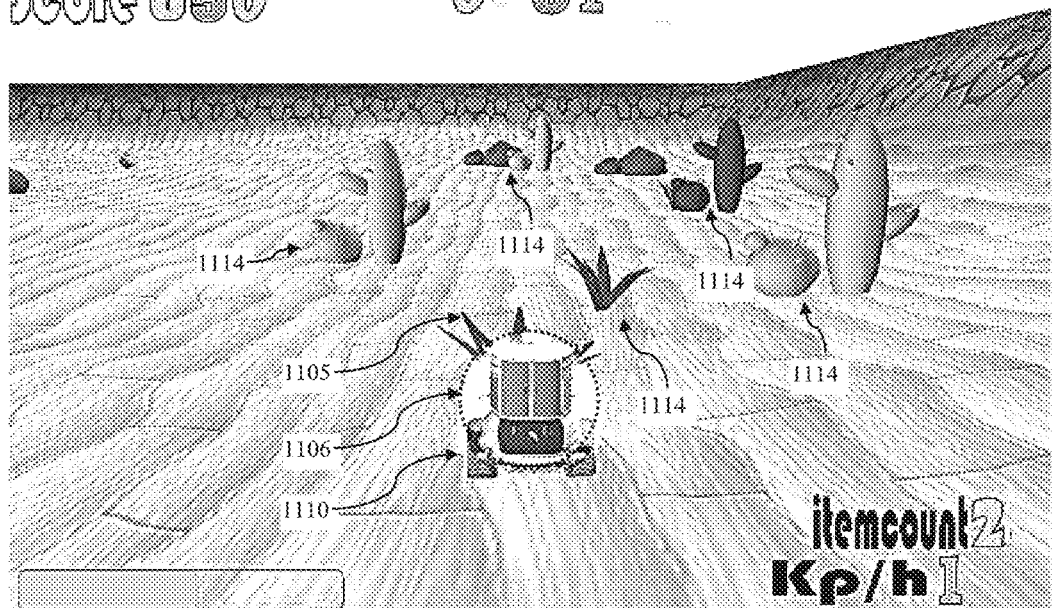
FIG. 11B is a screenshot of a therapeutic game according to another embodiment.

Another game is "Sunday driver" which is an infinite driver game. Drivers drive around looking for level specific items and a gold level transition door. Whilst driving they collect power up boxes which provide random effects, and they must avoid obstacles such as trees, rocks and seeker bombs that chase the driver. Driving over rough terrain causes haptic feedback, similarly crashing into objects causes particles to emanate from the collision area to form a collision cloud with associated haptic feedback used to reinforce the visual cue. The strength of the feedback can be context specific, and using the previous example, rough terrain could provide a sustained low intensity feedback level whilst over the rough terrain (s=0.2-0.5 depending upon the roughness) whereas a direct impact with an object could provide a large feedback signal (s=1.0). FIG. 11B is a screenshot from "Sunday Driver" illustrating a collision of the user's vehicle 1110 with a plant 1105. This collision causes particles to emanate from the collision area to form a white collision cloud designated by circle 1106 around the plant which persists whilst haptic feedback is provided. A plurality of obstacles 1114 are distributed throughout the driving terrain. Other game related data such as speed, item count and score may also be displayed.

Figure 11C:
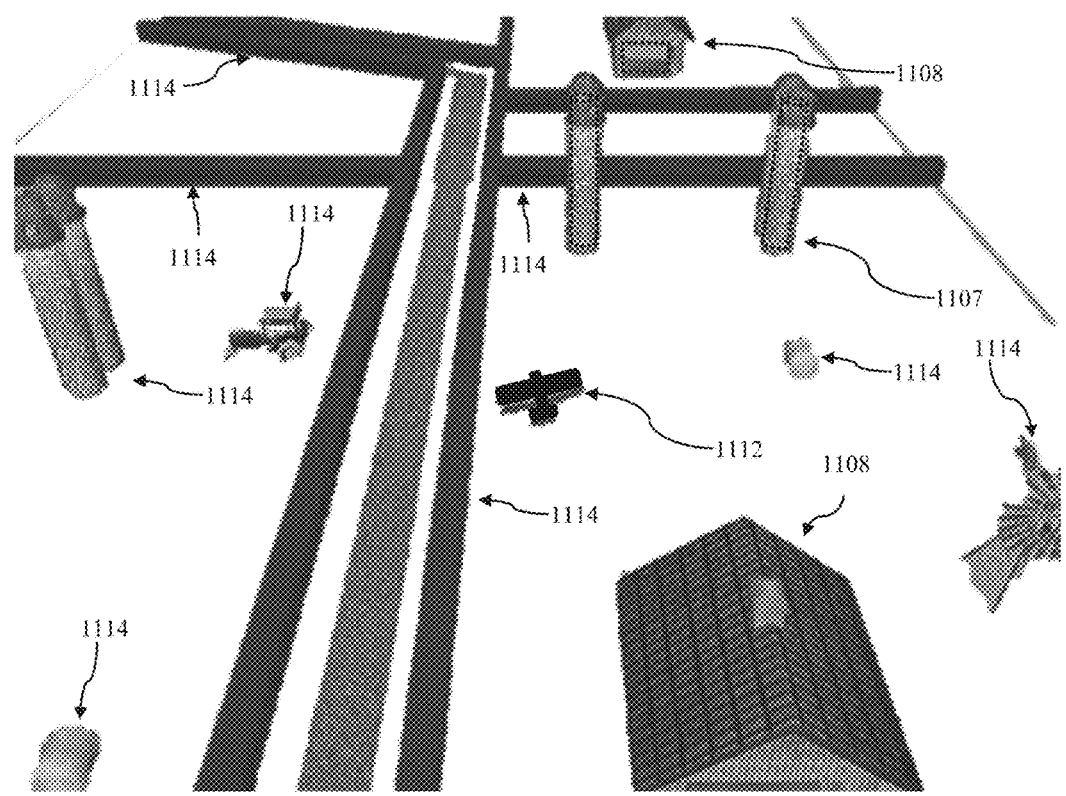
FIG. 11C is a screenshot of a therapeutic game according to another embodiment.

Another game is Biplane 1922, which is a flight simulation game with simple game mechanics constructed around the concept of Barnstorming, an early form of civil aviation. The game uses procedurally generated levels with a modular mission manager to provide variation to each game, and a unique difficulty system. Mission objectives vary from flying through open barns, flying between standing pylons or farm silos in a slalom race, as well as landing your aircraft at the end of each mission. Crashing into objects with the biplane is only lightly penalised —sufficient damage to the fuselage or both wings will eventually destroy the aircraft but the biggest result of crashing into obstacles is a decrease in the player's final score. Other tasks such as successfully landing, clearing pylons and how quickly each mission is completed influence the final score, but none prevent the player from carrying on to play new levels and unlocking new missions. Medals are presented to the player depending on their performance, with a score metric as a more detailed measure of their performance. Simply completing a mission will earn a player a bronze medal, with mathematically determined requirements for speed in completing a mission and percentage objectives successfully cleared unlocking silver and gold medals. In this way, players of all levels of skill and ability will be able to successfully complete missions and play through the entire game. Repeated play is incentivised with the ability to earn more valuable medals, attainable with greater precision and practice. To further improve the longevity of the game, camera angles are changed, which combined with procedural generation of levels leads to a different experience each time the game is played, maintaining interest and extending longevity. FIG. 11C shows an annotated screen shot of Biplane 1922 with the biplane 1112 approaching farm silos (outlined with cylinders 1107) and a barn (entrance outlined with rectangle 1108). A series of other obstacles 1114 such as roads, hedges, tractors, bales, and other structures are distributed throughout the playing environment. Haptic feedback can be provided if the biplane hits an obstacle, flies between silos 1107 (eg the silos form a gate), or through a barn 1108.

There are several metrics of success in Biplane 1922, and all are measured for analysis such as time taken, goals achieved and performance in landing. Like Space Stuntz, contextually-relevant haptic feedback is used extensively. Scoring events like passing through objectives provide small short vibrations (s=0.1), with collisions with obstacles producing much stronger ones (s=1). A steady vibration is also used while the biplane is on the ground (s=[0.0, 0.6]), with intensity dependant on travelling speed to emulate taxiing on a runway.

A pilot evaluation was conducted with a group of typically developing children who all had appropriate gaming experience and background. Most commercial gaming systems are inaccessible to children with CP, meaning they lack experience of the 'commercial expectation' of games. Consequently, using typically developing children to test the games means they were evaluated by a knowledgeable group for their content and appeal. A set of six trial games were designed and installed on a HP Pavilion dv7-6107tx Entertainment Notebook provided with a standard Xbox 360 USB controller used to interact with the games to allow testing of the games and gaming platform to ensure the games were fun, challenging, entertaining and enjoyable. In these trials all movement controls were assigned to the left thumb stick and all button presses to the "start" button. The six games were trialled with 31 typically developing children, aged 5-12 years. The set of children was divided into four different focus groups (from n=6 to n=9) and were given a 60 minute block of time in which to play. They were free to choose how many games they played and in what order. The games received very positive feedback in terms of game enjoyment (88%), game repeatability (85%), and overall game interest (73%). During the user evaluation, 74% of the responses indicated that the children would buy the game they were playing if it was in a store, indicating that they at least met commercial expectation. In some games haptic feedback was provided to both sides of the controller to test the vibration tolerance of users.

A further trial of nine games was performed by a 12 year old patient with CP who volunteered to provide critique and feedback over a 14 day period and game play was logged. For example, over the two weeks, Biplane 1922 was played a total of 10 times, for a total time of 43.9 minutes, with each session averaging 4.4 minutes in length. Of that time the participant spent on average 29.5 seconds in the menu system, with the remainder of the time spent playing the game. The longest session lasted for 6.8 minutes, and the shortest for 2.5 minutes. Only one game was played per session. In a post-evaluation, the participant reported thoroughly enjoying the pilot trial, preferring to play games on the system rather than engage in the patient's normal extra-curricular activities (competitive swimming). The pilot study demonstrated that the games were capable of promoting good levels of engagement and replay. Each of the games were typically played for no more than 4-5 minutes per session, but over the course of the 14 day trial period, the large number of different sessions played indicated a maintained interest in playing the games. This trial indicated that the games were accessible, fun, and enjoyable, confirming that the development process being used was appropriate. Feedback from the participant included statements that "the vibration of the controller when you hit something was very creative and easily felt" and that the patient "had the best 2 weeks of my life playing the games".

Figure 2:
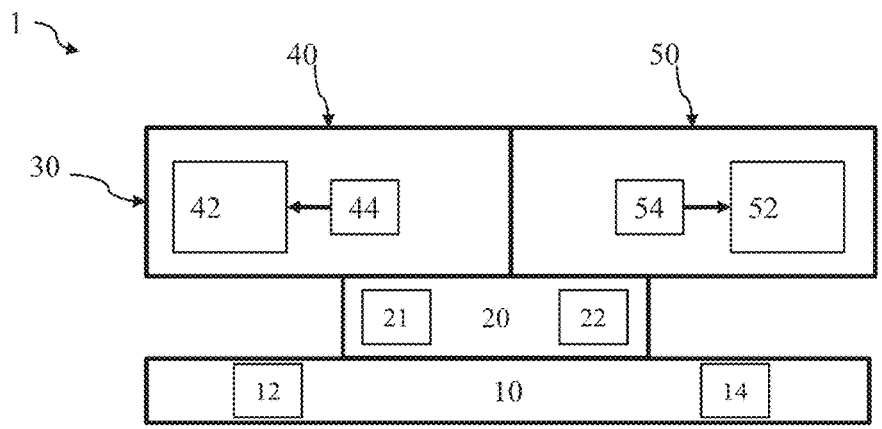
FIG. 2 is a schematic diagram of an input apparatus according to an embodiment.

Input apparatuses (devices) have also been developed to provide isolated haptic feedback in serious games. FIG. 2 shows a schematic diagram of an embodiment of the input apparatus 1. The input apparatus 1 is a two handed controller and comprises a base 10, a top section 30 and a mount 20 for mounting the top section 30 relative to the base 10. The mount allows the top section to move in two axes (or dimensions) relative to the base to define the input provided by the device. The mount further comprises a first axis sensor 21 and a second axis sensor 22 for measuring the movement of the top section in each axes. In one embodiment the controller is a pivoting controller. The input apparatus further comprises a first surface 42 on a first side 40 of the pivoting element for a first hand of the user and a second surface 52 on a second side 50 of the pivoting element for a second hand of the user. The input apparatus also comprises a first haptic actuator 44 to provide haptic feedback to the first haptic portion or surface 42 and a second haptic actuator 54 to provide haptic feedback to the second haptic portion or surface 52. In some embodiments, the first haptic portion may be the entire first side and the second haptic portion may be the second side. The input apparatus comprises at least one haptic actuator that can be used to selectively provide haptic feedback to the first or second haptic portion. In one embodiment the input apparatus comprises a first haptic actuator for providing haptic feedback to the first haptic portion and a second haptic actuator for providing feedback to the second haptic portion. In one embodiment the first side is isolated from the second side and in another embodiment the first and second surfaces are mounted in their respective sides using isolation mounts 38 so that the haptic feedback can be provided independently to the first and second surfaces 42 52 to prevent or substantially minimise transfer of haptic feedback (vibrations) from one side to the other. That is, the isolation mounts are configured or include materials to dampen vibrations so that any cross vibration effect is prevented or minimised in order to avoid or reduce sensory extinction. In some embodiments, the shape of the controller and location of the haptic surfaces in the respective sides of the controller are selected to provide haptic feedback to the fingers and palm of each hand.

In some embodiments, the first and second surfaces are each textured to enhance or heighten the haptic feedback. Texturing may include making the surface rougher or providing projections or dimples in the surface. Texturing may also include creating raised portions, ribs, hollowed sections, or surface contours for finger pads and palm that may have a dual use to indicate where to place fingers and palm.

These haptic feedback surfaces 42 52 could be made of a different material to the rest of the controller, such as a different plastic or rubber and may act to amplify haptic vibrations to maximise delivery to fingers and palms of the user. In another embodiment the first and second surface may be adapted or constructed to receive replaceable pads. For the sake of clarity, when attached, the pads will transmit haptic feedback to the hand, and effectively form part of the haptic feedback surface. These replaceable pads could clip on, be screwed on, or attached via magnets or other arrangements. Providing replaceable pads allow them to be removed for cleaning or in case surface texturing wears down or becomes less effective through use. Alternatively, the pads may be permanently fixed (eg glued or fastened) in place. Texturing may also be applied to the first side and second side, and different texturing may be applied to the first and second sides and the first and second surfaces.

Figure 3A:
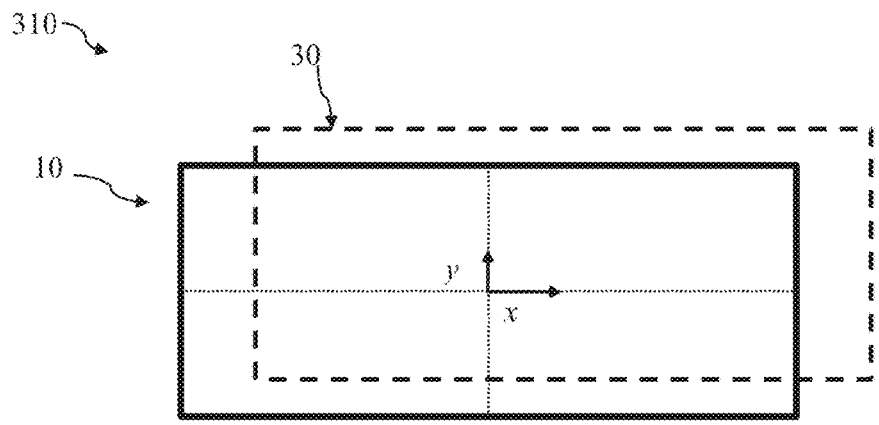
FIG. 3A is a schematic top view of a top section mounted to a base via a translation mount according to an embodiment.
Figures 3B, 3C:
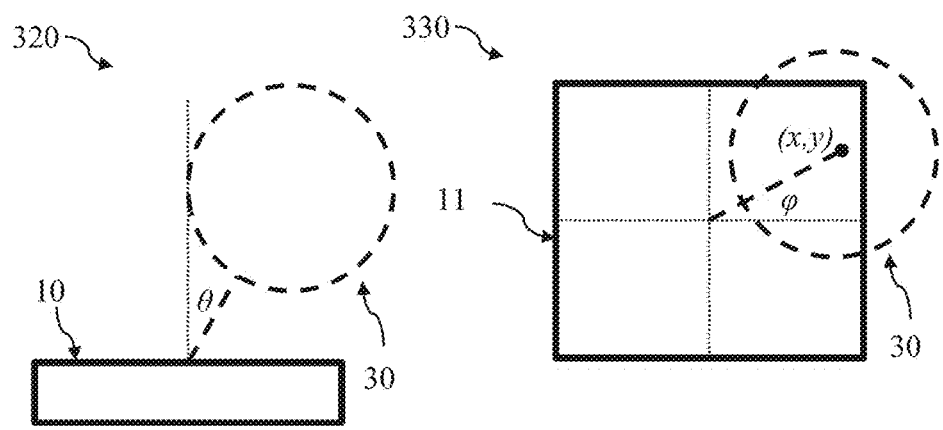
FIG. 3B is a schematic side view of a top section mounted to a base via a pivotal mount according to an embodiment.
FIG. 3C is a schematic top view of a top section mounted to a base via a pivotal mount according to an embodiment.

The mount allows the top section to move in two axes (or dimensions) relative to the base to define the input provided by the device. FIG. 3A is a schematic top view 310 of a top section 30 mounted to a base 10 via a translation mount and FIGS. 3B and 3C are schematic side 320 and top 330 view of a top section 30 mounted to a base 10 via a pivotal mount. In FIG. 3A the mount 20 is a translational mount allowing the top section 30 to move within a plane parallel to the base 10 defined by an X axis and a Y axis, and the translation mount is configured to measure the X and Y positions within the plane. In FIG. 3A the top section has translated to a position x, y relative to the zero position. The x and y positions can be measured using separate linear potentiometers or linear encoders which track movement of the top section relative to the base (ie a first linear potentiometer is used for reporting an X position within the plane and a second a second linear potentiometer is used for reporting a Y position within the plane).

FIG. 3B is a schematic side view 320 and FIG. 3C is a schematic top view 330 of a mount that allows pivotal movement of the top section 30 relative to the base 10, similar to an analogue joystick (or analogue stick). In this embodiment, the mount includes sensors for detecting and measuring the zenith angle θ and azimuthal angle φ of the top section relative to an axis normal to a plane parallel to the base. A position detection circuit may comprise a first and a second potentiometer for measuring the zenith and azimuthal angles respectively or encoders may be used. These angles can be projected onto an x, y position in a plane parallel to the base with the projection performed either in hardware or software. The mount may be configured to self-centre the top section over the base. This may be achieved using spring or elastic members to bias the top section to a central position. For example, the pivotal mount and sensors from a Logitech Attack 3 Joystick may be used.

In one embodiment, the first haptic actuator is mounted in a horizontal orientation in the first side and located to maximise the travel path between the actuator (the source of vibrations) and the mounting location of the first side to a central mounting portion of the top section. Rubber isolation mounts are used to mount the first side to the central mounting portion to further dampen and prevent transfer of vibration signals from the first side to the second side. A similar arrangement is used for the second side. In another embodiment the first haptic actuator is mounted under the first surface to form a first haptic module, and the first haptic module is mounted in a haptic module mount in the first side. The haptic module mount further comprises a first isolation component for isolating haptic vibration from the haptic module to the first side. A similar arrangement is used for the second side. The haptic actuators may be a small motor with an unbalanced mass on the drive shaft to generate vibrations. For example, the haptic actuator from an Xbox 360 controller may be used. The motor may be mounted in a vertical orientation in which the axis of the drive shaft is vertically directed (ie normal to the plane containing the base) or in a horizontal orientation in which the axis of the drive shaft is horizontally directed (ie parallel to the plane containing the base). The isolation components used in the mounts may be vibration or energy absorbing materials such as foams or rubber.

Preferably, the isolation material should significantly reduce the transfer of the vibrations whilst not significantly dampening the haptic signal. Choice of isolation material will depend upon the specific design, and various materials can be tested and trialled once the approximate design such as location of haptic motors and arrangement for transferring vibrations (haptic feedback) to the haptic surfaces have been assessed. Isolation materials that can be used include Acoustic Foam, Enduro Foam, High Density Foam, PE30, EVA 30, EVA 75, EPDM sponge (3 mm and 4.5 mm thick), natural rubber, rubber weather strip or other rubber materials.

The input apparatus may be constructed using a variety of designs. Generally the first surface and the second haptic portions are located to maximise delivery of haptic feedback to the patient's fingers and palms. In some embodiments the first and second sides are concave and are arranged relative to each other such that in use a user is required to contact both the first and second surfaces to hold and pivot the controller. That is, two handed movement is required for control of the controller. In another embodiment the first and second surfaces are constructed as grips. Further design considerations are that the controller should require two hands to control and move, and ridges or valleys between the first and second controller should be large enough to prevent a user from one handed control of the controller. To assist in ensuring that a user is able to keep a hand over the first or second surface (as required), respective first and second straps may be provided for the first and second surfaces. Many CP patients have poor motor control of the hand affected by sensory agnosia, and thus a strap may be used to ensure contact of the fingers and/or palms with the surface delivering haptic feedback. In one aspect the straps are removable straps. To ensure compliance by the user, the controller can additionally comprise a first proximity detector for detecting if a hand is placed on the first surface, and a second proximity detector for detecting if a hand is placed on the second surface. The sensors may be infrared sensors mounted in the haptic surfaces or other sensors such as acoustic, electromagnetic or capacitive (touch) sensors. Software can be configured to pause a game, or only allow play when both hands are detected as being over the sensors.

The controller further comprises an input actuator 12, such as a button, touch or proximity sensor, that may be located anywhere on the controller except on the first or second surfaces, and an internal control or control and communications board 14 for providing the position of the top section of the controller (eg from sensors 21 and 22) to an external device (such as a computer) and for receiving signals to trigger haptic feedback. Additional input buttons may be provided if desired. These could be integrated into existing components such as by making the hand pads or haptic surfaces clickable. A haptic select switch could be provided in the base, for selecting which haptic portion the haptic feedback is to be provided to. The control and communications board 14 may communicate with an external device via wired or wireless protocols. The control board may include a microcontroller, microprocessor, memory or other circuitry for enabling selective provision of haptic feedback to the first haptic portion or the second haptic portion and for driving the haptic actuators. The control board may store the haptic mode (ie which side to provide haptic feedback to), or and include instructions or hardware to interpret a haptic select mode command sent to the controller (eg from the computing device) and to store and enable the selection. The control board may contain instructions or hardware to convert a haptic feedback signal, or commands into appropriate signals for driving the haptic actuators, such as into a pulse width modulated power signal provided to a motor in a haptic actuator. The haptic feedback signals could simply define haptic parameters (eg intensity and duration) that are interpreted by the control board, or predefined codes could be sent (eg different code values correspond to different intensity and duration values). Alternatively, the controller could simply receive a signal indicating the intensity level which is converted to an appropriate power signal for the controller whilst the signal is present. Alternatively, the control board 14 could simply act as a pass through for actuator controls signals sent from the computing device, ie the received signals are used to drive the haptic actuators. A battery and recharge port may also be provided. In one embodiment the control board from an Xbox 360 controller was adapted for use by replacing the trimpot outputs from the first analogue stick with the output of the potentiometers from the mounting arrangement and replacing one of the Xbox 360 buttons with the input button 12. The haptic actuators may also be used. The Xbox 360 comprises a large and small haptic actuator and so the small haptic actuator was replaced with a second large haptic actuator from a second Xbox 360 controller, to ensure uniform haptic feedback to either side. Use of an Xbox 360 as a basis facilitates communication with the controller using standard Xbox 360 communications protocols. Alternatively, other standard or propriety communications protocols may be used.

Figure 4A:
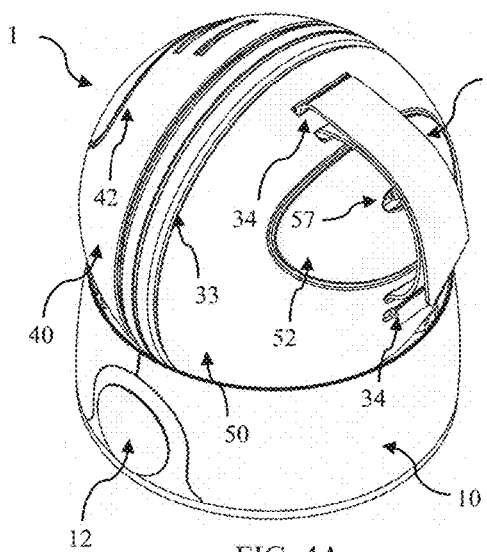
FIG. 4A is an isometric view a controller according to an embodiment.
Figure 4B:
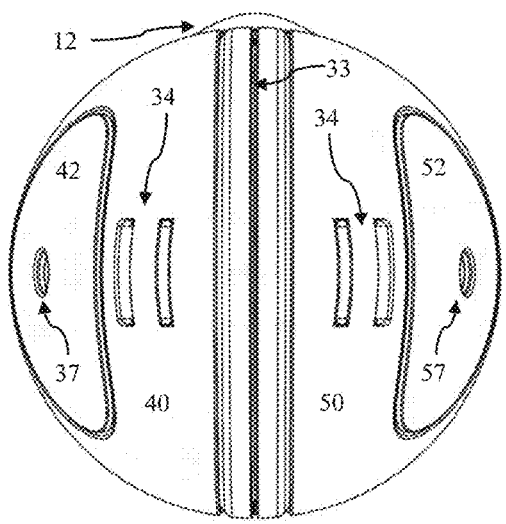
FIG. 4B is a top view of the controller illustrated in FIG. 4A.
Figure 4C:
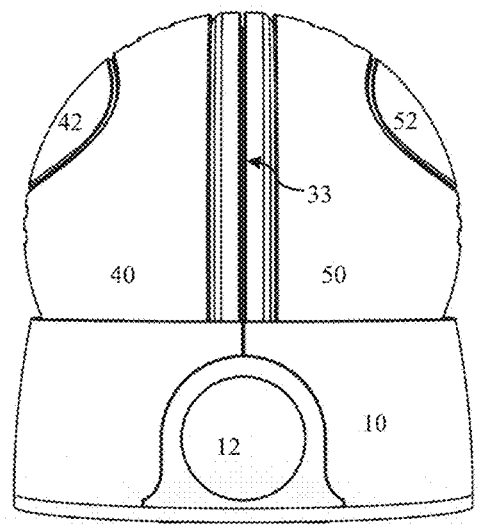
FIG. 4C is a front view of the controller illustrated in FIG. 4A.
Figure 4D:
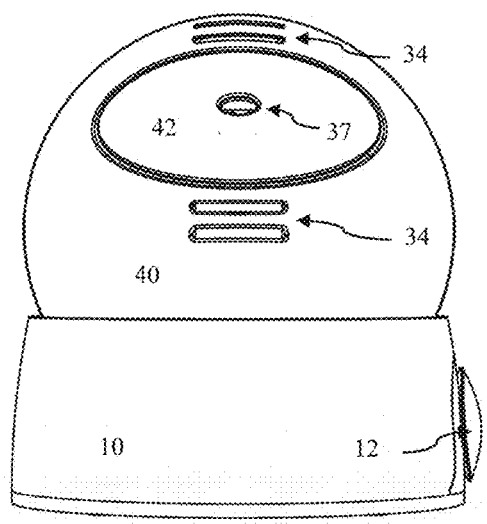
FIG. 4D is a side view of the controller illustrated in FIG. 4A.

Several embodiments of an input apparatus will now be described. FIGS. 4A to 4D are an isometric view, top view, front view and side view respectively of a spherical (or orb) controller according to an embodiment. FIGS. 4E and 4F are an isometric and top view of a variant of this embodiment. The spherical controller has a base 10 with an input button 12, with an internal pivoting mount for supporting the top section 30. The top section has a central axis 33 which divides the top section into a first side and a second side. Each side includes removable mounts for receiving an end of a strap. The strap is fed through a two sets of two slots 34 located respectively in the top and bottom of the first or second side about first and second surfaces 42 52 and the strap 60 is then pulled back over itself and strapped in place using matching Velcro parts. In this embodiment, haptic feedback is provided to the entire first side 40 by a first haptic actuator 44 and to the entire second side 50 by a second haptic actuator 54. The first and second sides each have, respectively, a first surface 42 and a second surface 52 that are large elliptical regions in the upper quadrant of each side and are sized to allow a user's palm and fingers to be placed over them. In this embodiment, the first and second surfaces are glued in place and are surface textured to increase the haptic feedback to fingers and palms. The mounts 34 for the strap 60 are located above and below each surface to ensure the patient's hand sit over the target surface. Additionally a first proximity sensor 37 is located in the first surface 42 and a second proximity sensor 57 is located in the second surface 52.

A variant of this embodiment is shown in FIGS. 4E and 4F. In this embodiment, the straps are secured using a mounting slot 34 on the central axis 33 and mounting points located below the first and second surfaces 42 52. In this embodiment, the first and second surfaces are mounted, respectively, in the first and second sides using isolation mounts 38, and haptic feedback is separately provided to each of the first and second haptic surfaces only (ie rather than the entire first and second sides as in FIGS. 4A to 4D).

Figure 5B:
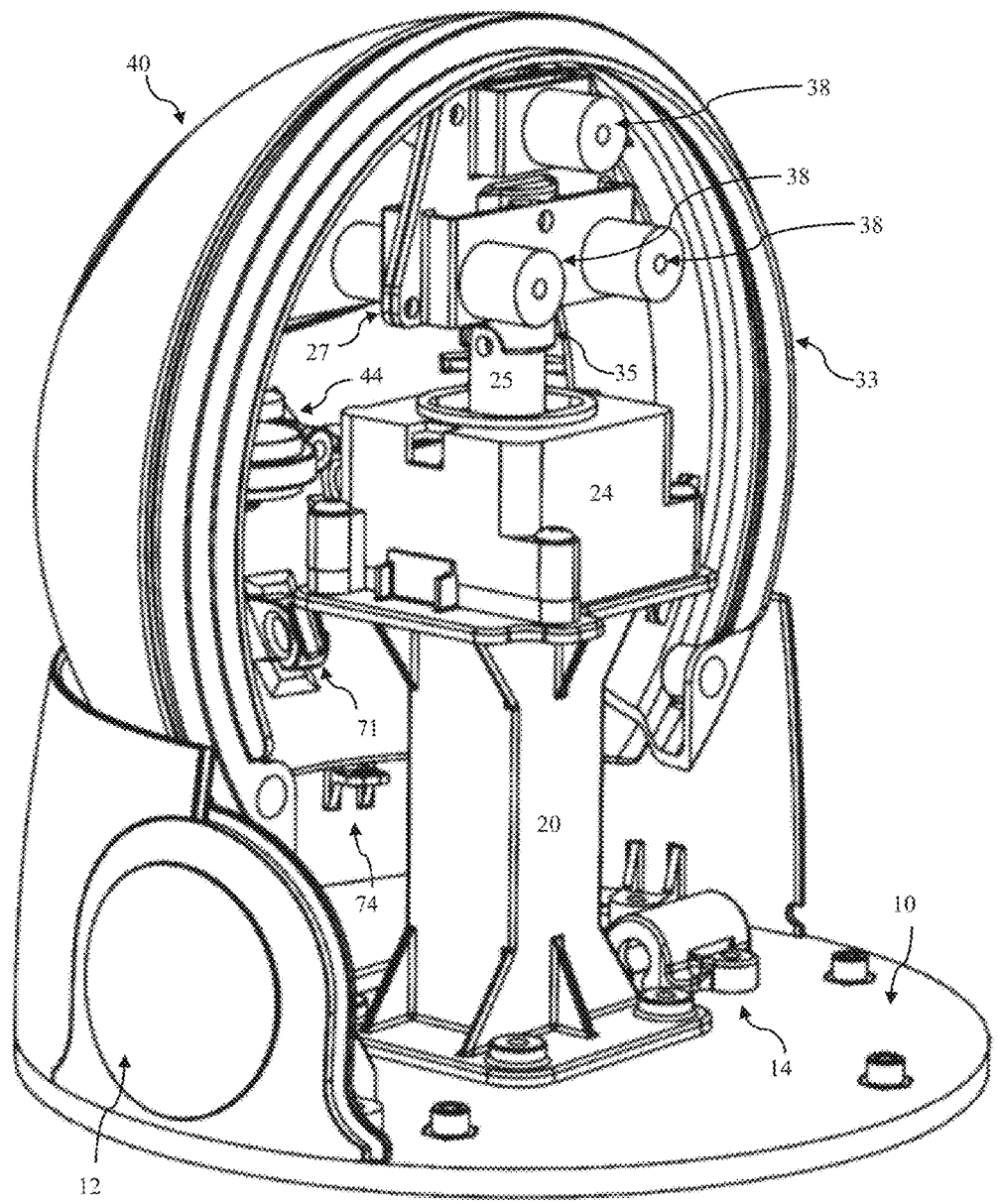
FIG. 5B is a isometric view of the controller illustrated in FIGS. 4A to 4D with the second side and part of the base removed.
Figure 5C:
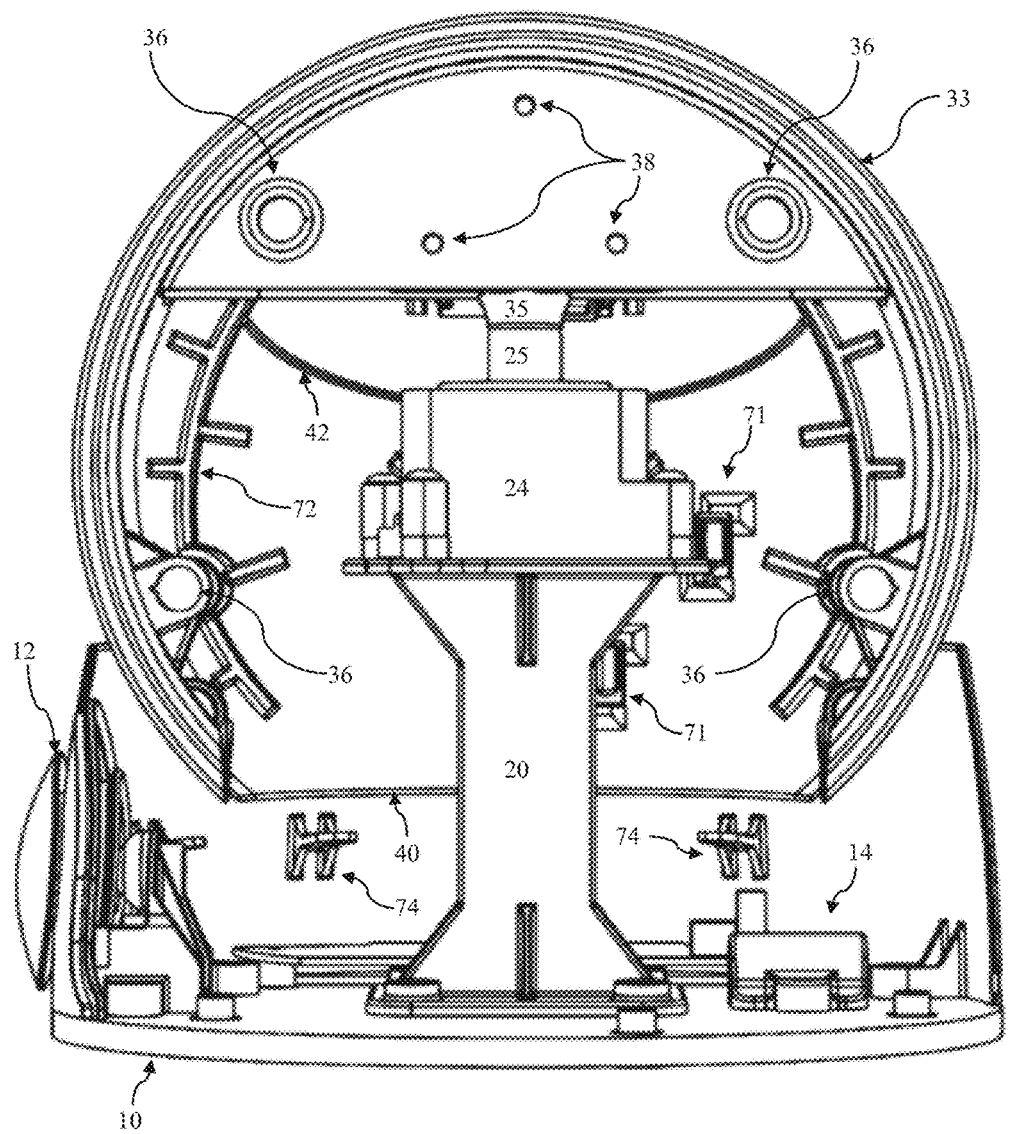
FIG. 5C is a first sectional view and FIG. 5D is a second orthogonal sectional view of the controller illustrated in FIGS. 4A to 4D.
Figure 5D:
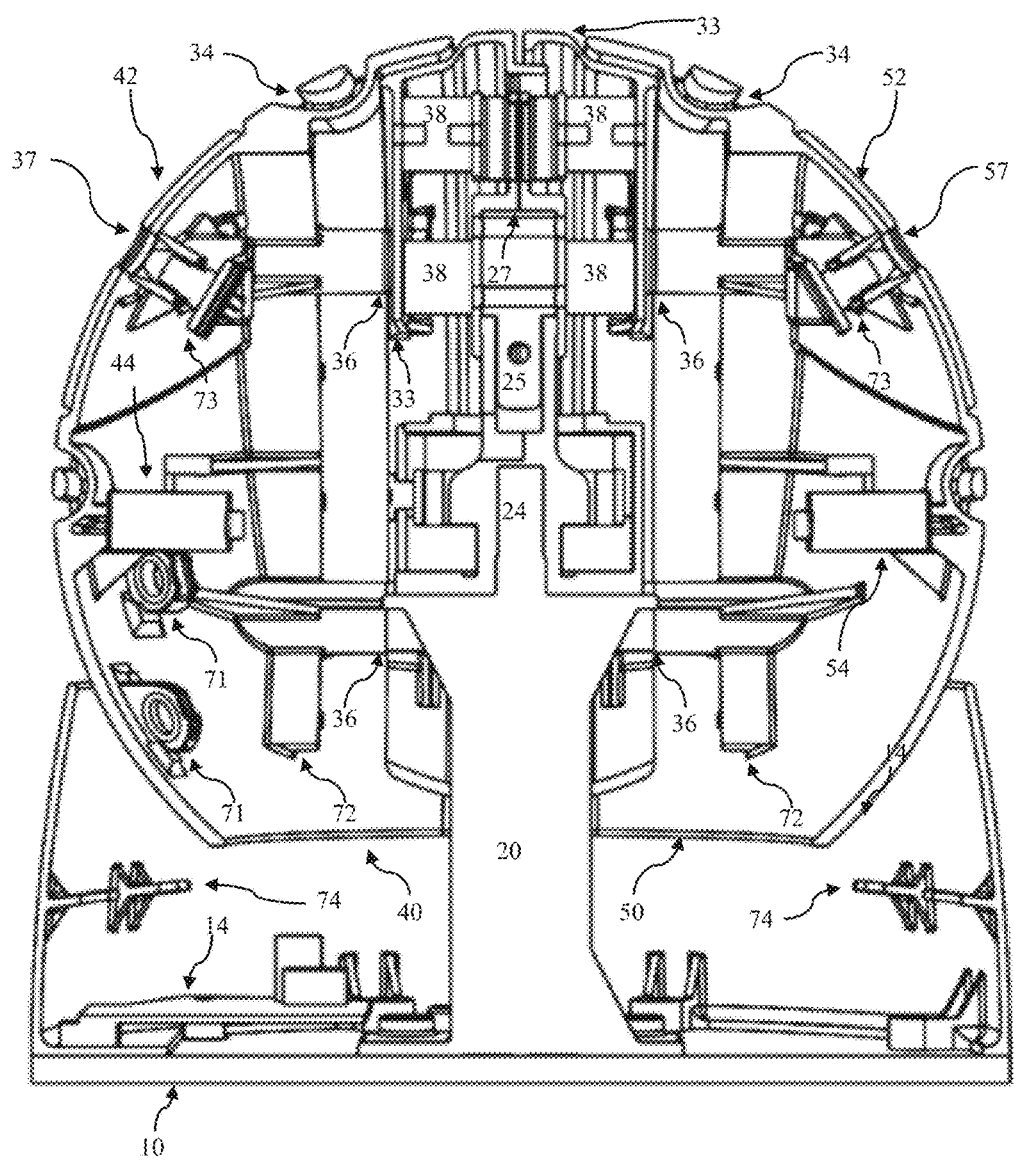
Figure 6A:
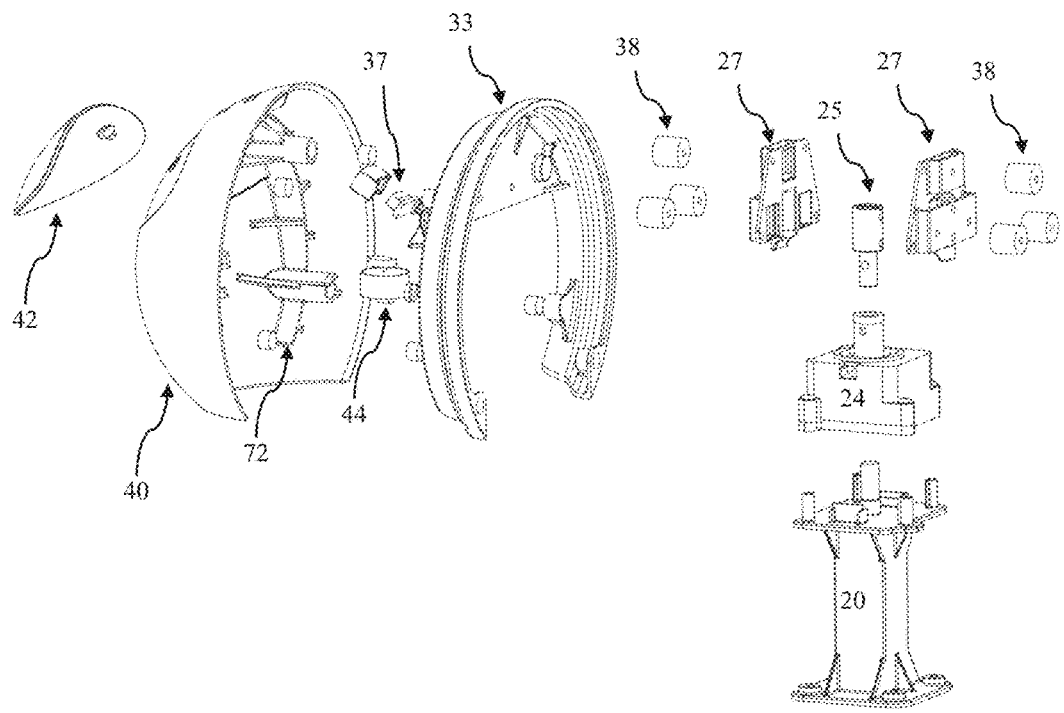
FIG. 6A is an exploded isometric view of a first side of the controller illustrated in FIGS. 4A to 4D.
Figure 6B:
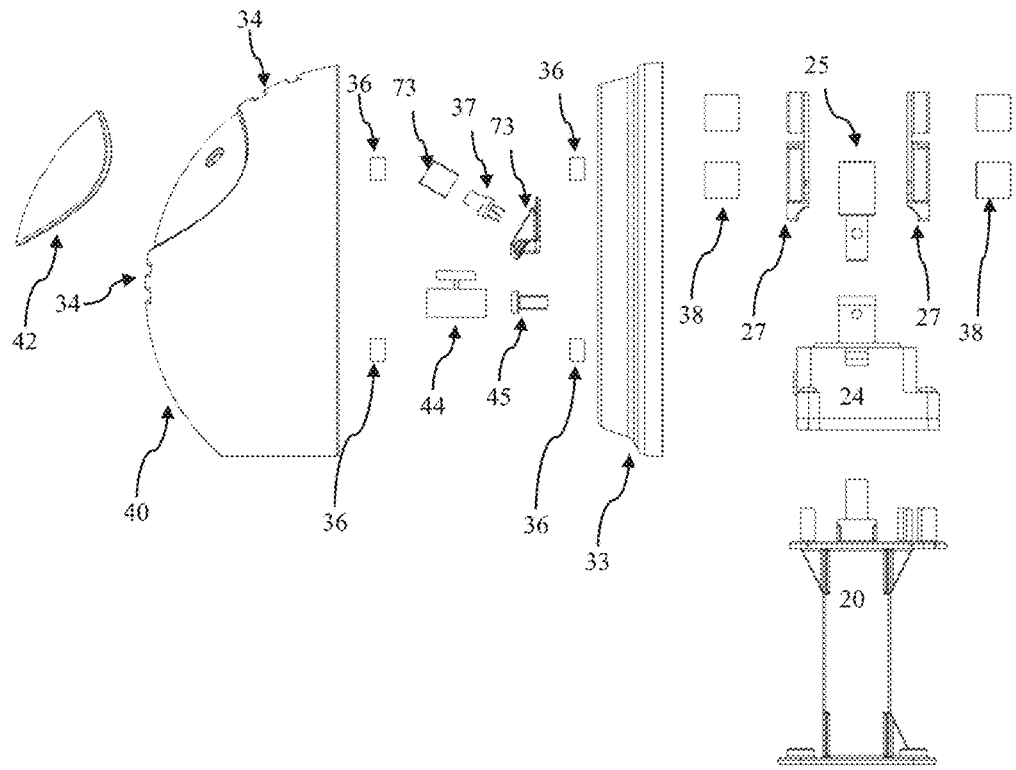
FIG. 6B is an exploded side view of a first side of the controller illustrated in FIGS. 4A to 4D.

FIG. 5A is an internal side view of a first side of the controller illustrated in FIGS. 4A to 4D, FIG. 5B is a isometric view of the controller illustrated in FIGS. 4A to 4D with the second side and part of the base removed, FIG. 5C is a first sectional view and FIG. 5D is a second orthogonal sectional view of the controller illustrated in FIGS. 4A to 4D. FIG. 6A is an exploded isometric view of a first side of the controller illustrated in FIGS. 4A to 4D and FIG. 6B is an exploded side view of a first side of the controller illustrated in FIGS. 4A to 4D.

As can be seen in FIG. 5A, the first side 40 comprises a first surface 42 in the shape of an ellipse. The exterior of the first surface 42 is textured to increase haptic feedback and includes a first proximity sensor 37 mounted in a proximity sensor mount 73. A haptic actuator 44 is mounted in haptic mount 45 located in the interior of the first side, just below the bottom of the first surface 42. A series of cable loops 71 are provided in the interior side wall to guide the control and power supply cable/wires for the haptic actuator and proximity sensor. A support structure 72 extends outwards from the interior surface of the side wall, and includes a plurality of magnets 36 for mounting the first side to a first central axis portion 33. The first central axis portion 33 has an extended arc structure matching the perimeter of the first side and includes reciprocal magnets or magnetically sensitive material 36 to engage with the magnets in the first side. Other arrangements could be used to secure the first side to the first central axis portion. The first central axis portion 33 has a plate like section in the top section which is used to mount the first central axis portion 33 to the central stem plate 27 using a triangular arrangement of three tubular rubber isolation mounts 38 The rubber isolation material are cylindrical tubes of natural rubber, although a other shapes could be used (eg rectangular or hexagonal cross sectional profile), or the isolation material could be a solid block. The exact dimensions (eg length, diameter, wall thickness) can be varied as required to suit the specific design to ensure/maximise dampening or transfer of vibrations across the isolation mount. The central stem plate 27 extends up from a hollow shaft 35 that is located over the central axis 25 that extends up from pivoting mount 24. A similar arrangement is used on the second side. This design maximises the travel path of vibrations (haptic feedback) from the source in the side wall to the mounting points on the central stem plate 27. The use of a minimal set of rubber isolation mounts 38 further acts to minimise transfer of haptic feedback from one side to the other (one hemisphere to the other hemisphere). Additionally the base 10 includes a plurality of LED supports 74 that are used to support LED lights that illuminate the bottom edge of the sides (ie the rim) to indicate the controller is powered on. The base 10 includes an internal control and communications module or circuit board 14. A battery may also be located in the base 10 if the controller is a wireless controller. The haptic actuators may be obtained from or similar to those in an Xbox 360 controller. The central axis 25 and pivoting mount 24 may be sourced from a Logitech Attack 3 joystick or similar joystick.

Figure 5E:
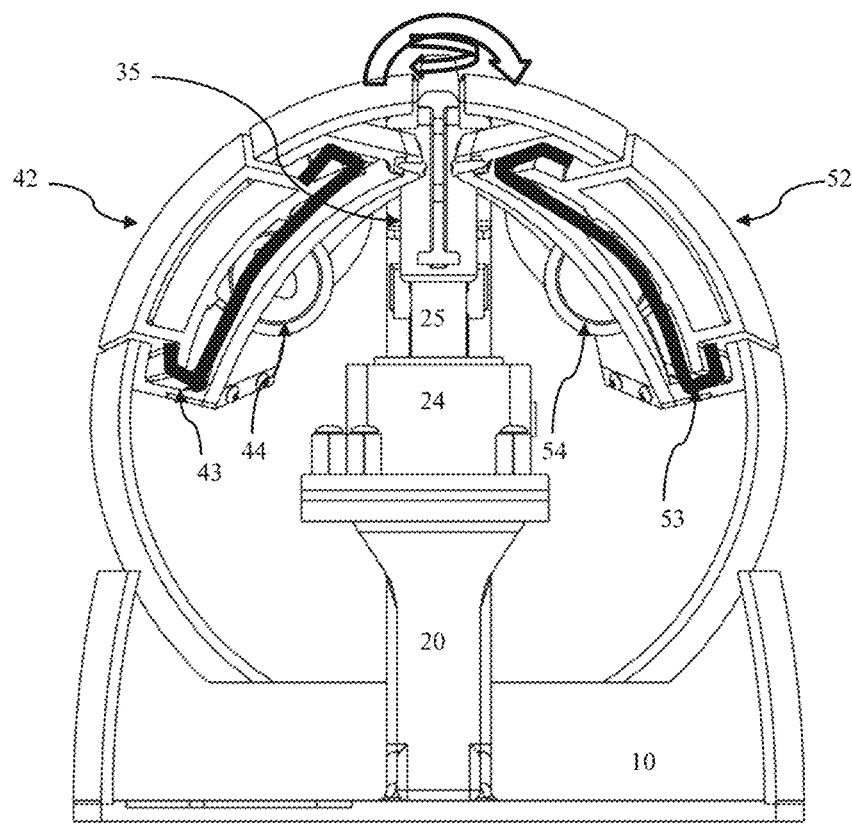
FIG. 5E is a first sectional view and FIG. 5F is a second orthogonal sectional view of the controller illustrated in FIGS. 4E and 4F.
Figure 5F:
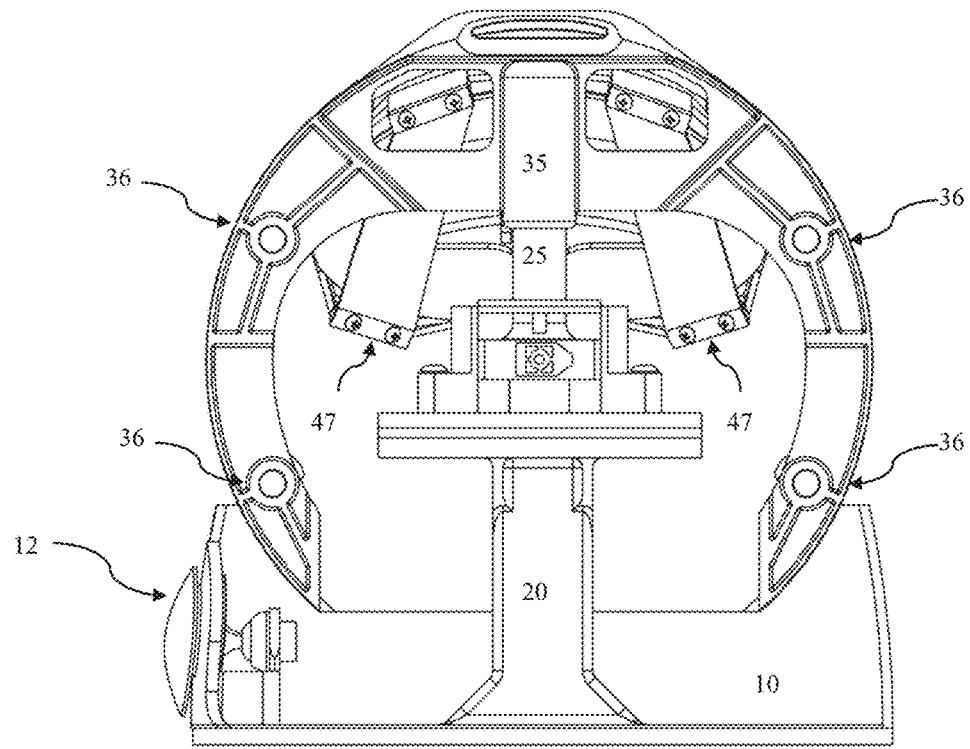
Figure 6C:
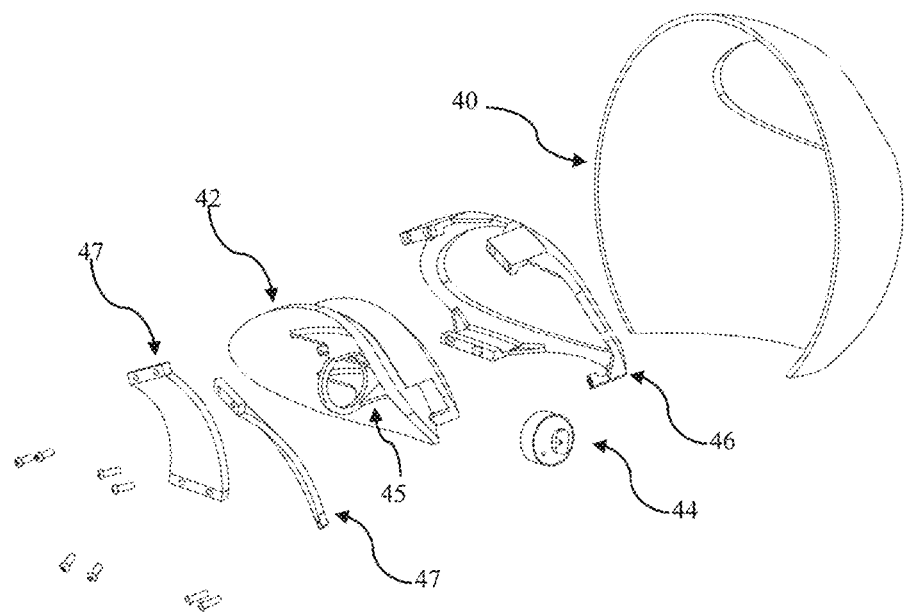
FIG. 6C is an exploded isometric view of a first side of the controller illustrated in FIGS. 4E and 4F.
Figure 7A:
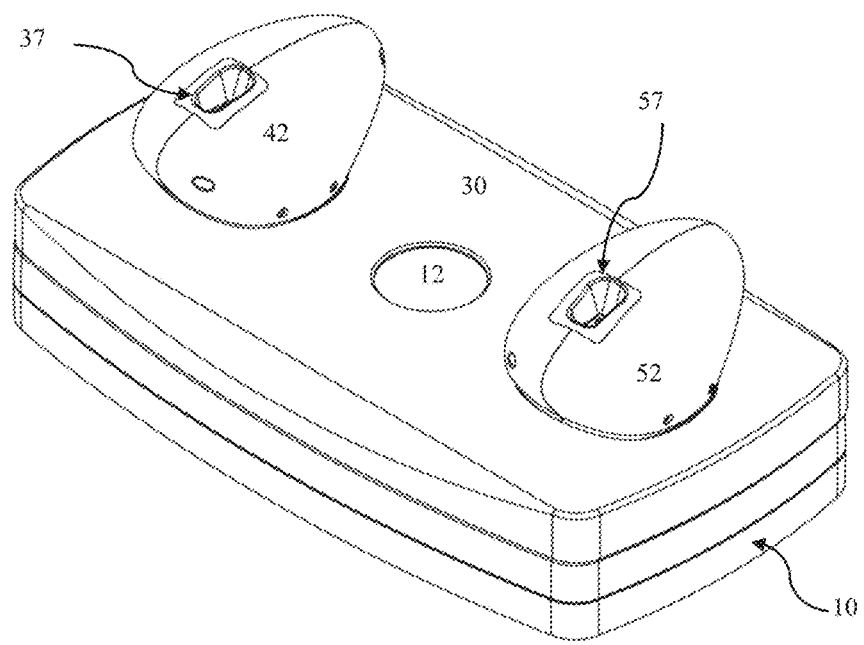
FIG. 7A is an isometric view of a controller according to another embodiment.
Figure 7B:
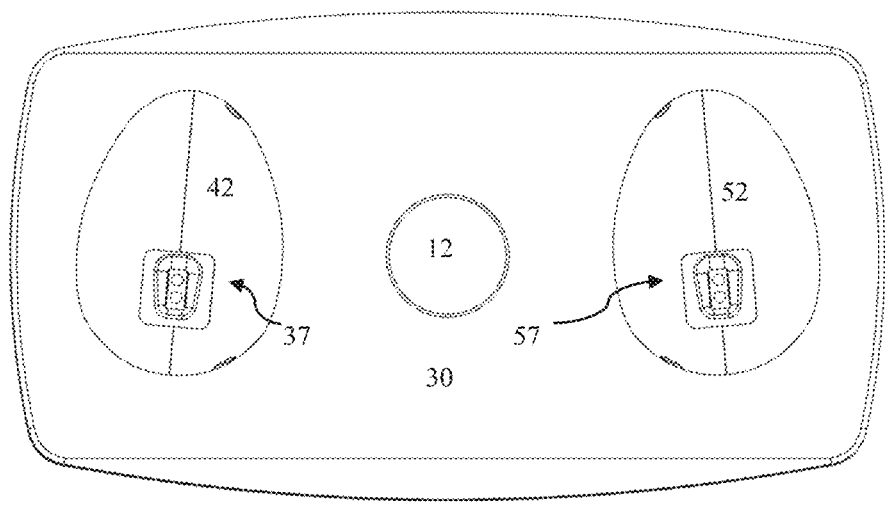
FIG. 7B is a top view of the controller illustrated in FIG. 7A.
Figure 7C:
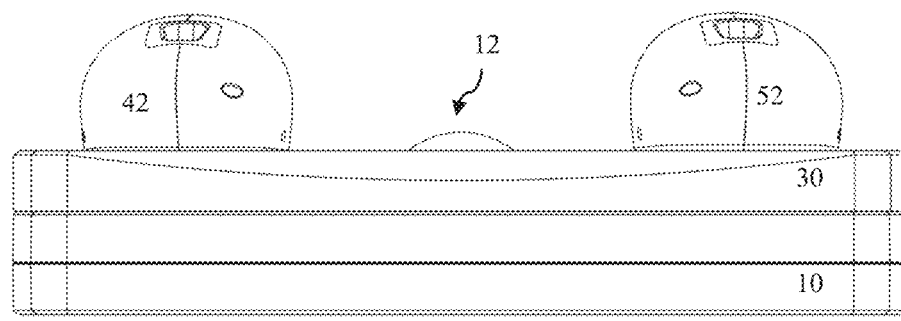
FIG. 7C is a front view of the controller illustrated in FIG. 7A.
Figure 7D:
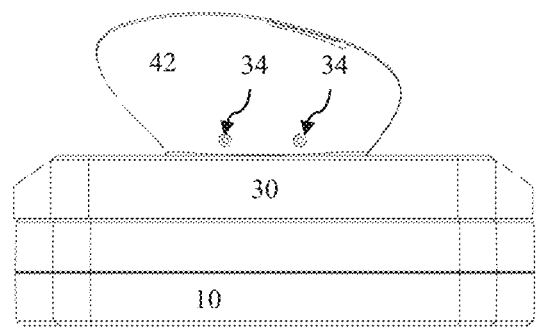
FIG. 7D is a side view of the controller illustrated in FIG. 7A.

FIG. 5E is a first sectional view and FIG. 5F is a second sectional view of the controller illustrated in FIGS. 4E and 4F. As can be seen in FIGS. 5E and 5F, the mount 20 comprises a pivoting mount 24 with a central axis 25 which is sourced from a Logitech Attack 3 joystick. This is mounted directly in the centre of the dome to provide spherical control. The top section includes a hollow shaft 35 which is placed over the central axis 25 (ie over the joystick). The two sections are clipped onto the central axis 35 using magnets 36. FIG. 6C is an exploded view of a first side of the controller illustrated in FIGS. 4E and 4F illustrating the haptic module. As can be seen in FIGS. 5E, 5F and 6C, each (haptic) surface 42 52 includes a haptic mount 42 for receiving a haptic actuator 44 in the form of a motor with a weight located on the drive shaft. The haptic actuator was sourced from an Xbox 360 controller. In this embodiment, the controller is horizontally mounted, but it could also be vertically mounted. The haptic mount 42 is sandwiched between an outer housing 46 and inner securing plates 47. An isolation material such as high density foam is located in the gaps 43 between the haptic mount and the outer housing 46 and inner securing plates 47 so as to substantially isolate the haptic module from the top section. The control and communication electronics board is located in the base of the controller (not shown). The spherical design maximises use through accommodating different hand sizes (small hands through to large hands).

Figure 8A:
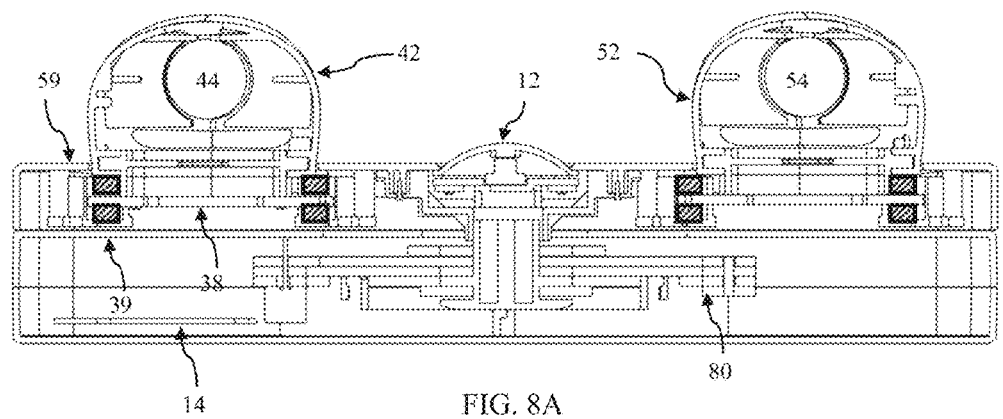
FIG. 8A is a first sectional view of the controller illustrated in FIGS. 7A to 7D.

FIGS. 7A to 7D are an isometric view, top view, front view and side view respectively of another embodiment of a controller using a translational mount. The top section 30 is moveable (translatable) in a plane parallel to the base 10. The first and second haptic surfaces are provided as grips 42 52, which are spaced apart from each other by a distance greater than a typical arm width and each mounted within a top section. An input button 12 is placed between them. IR proximity sensors 37 and 57 are located in the rear top section of the grips to detect a palm placed over the grip. Apertures for receiving a strap 60 are also shown on the side of the grips FIG. 8A is a first sectional view of the controller illustrated in FIGS. 7A to 7D and FIG. 8B is an isometric view of a first grip of the controller illustrated in FIGS. 7A to 7D. The base of the grip is an isolation mount 38 in the form of a plate with C shaped mounts 59 extending above and below the plate to create cavities 58 to receive the isolation material 39. The C shaped mounts are filled, both above and below the plate with an isolation material 39 such as high density foam, and the mounts are secured to the bottom surface of the top section. The base also contains an electronics board 14.

Figure 8B:
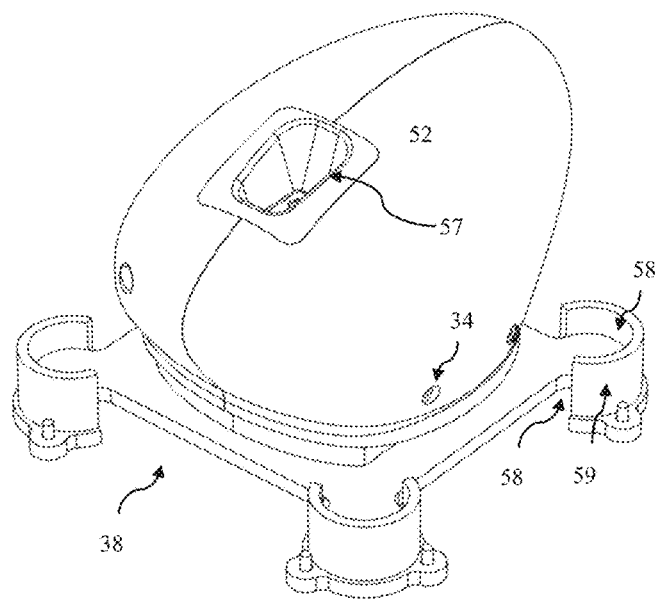
FIG. 8B is an isometric view of a first grip of the controller illustrated in FIGS. 7A to 7D.
Figure 8C:
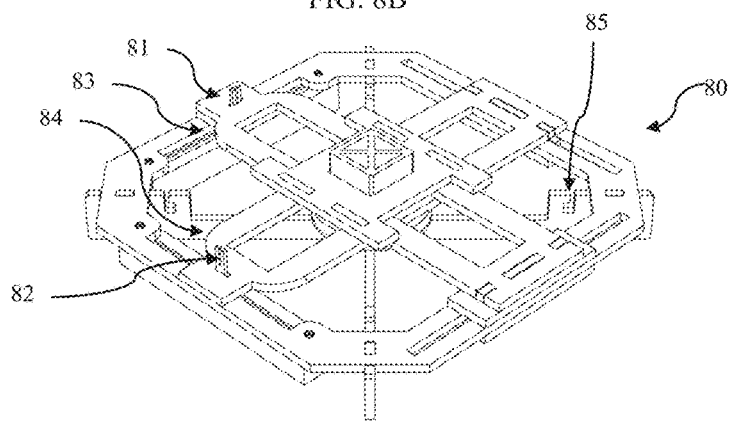
FIG. 8C is an isometric view of a translational mount illustrated in FIG. 8A.

FIG. 8C is an isometric view of a translational mount 80 using linear potentiometers 81 82. This is located in the centre of the top section under the input button 12. The translation mount comprises two orthogonal frames 83 84 with central apertures. A post from the top section extends down and through both apertures. The frames allow lateral movement in X and Y directions (but not rotation) and the position is measured using linear potentiometers 81 82 on the respective frames. The mount also comprises a self-centering mechanism comprising an X shaped member 85 (45 degrees to the X and Y frames) with a series of hooks and elastic members which are placed around the base of the post.

Figures 9A, 9B:
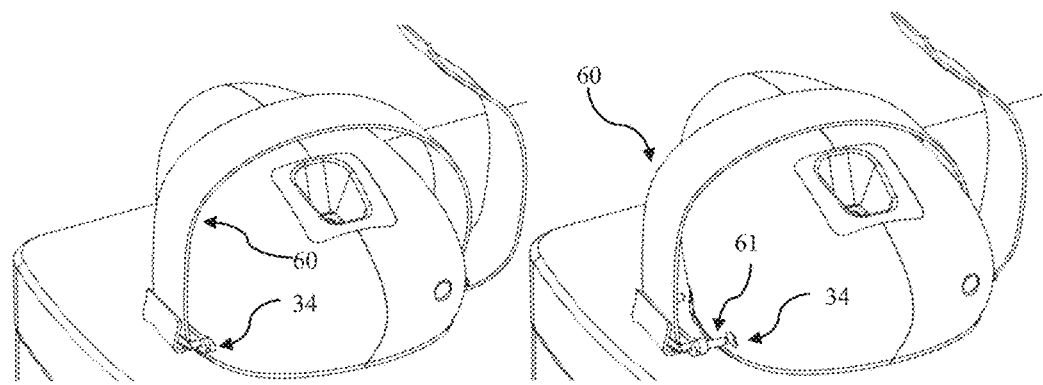
FIG. 9A is an isometric view of strap inserted into the side of the first grip illustrated in FIG. 8B
FIG. 9B is an isometric view illustrating removal of the strap from the side of the first grip illustrated in FIG. 8B.

A strap may be fitted to either grip. Each hand grip further comprises apertures 34 for receiving projections from a strap. FIG. 9A is an isometric view of strap 60 inserted into the side of the first grip illustrated in FIG. 8B and FIG. 9B is an isometric view illustrating removal of the strap 60 from the side of the first grip illustrated in FIG. 8B. One end of the strap 60 is fixed to the projections 61 which insert into apertures 34, and the other end uses a loop section to allow the strap to be tightened or loosened as required to secure or release a hand.

Figure 10:
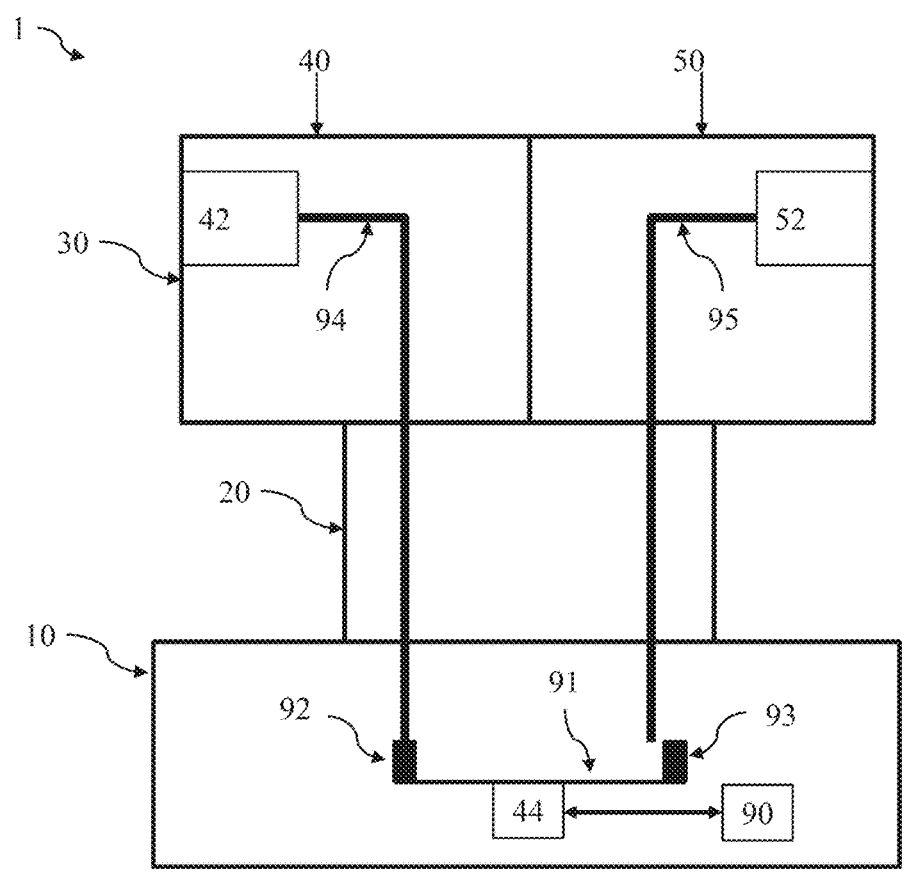
FIG. 10 is a schematic view of a controller according to an embodiment.

FIG. 10 is a schematic view of a controller according to an embodiment. In this embodiment, a single actuator 44 is mounted to a beam 91 that can be translated or moved between one or two positions by a motor 90. The beam comprises a first connector 92 at one end of the beam and a second connector 93 at the other end of the beam. The first connector 92 is for connecting with a first haptic feedback transfer structure 94 for propagating haptic feedback (vibrations) to a first surface 42. Similarly, the second connector 93 is for connecting with a second haptic feedback transfer structure 95 for propagating haptic feedback (vibrations) to a second surface 52. The first connector 92 and second connector 93 are located on beam 91 in an offset arrangement. In a first position, the first connector 92 engages with and connects to first feedback transfer structure 94, whilst the second connector 93 is not connected to the second feedback transfer structure 95. In a second position, the first connector 92 is not connected to the first feedback transfer structure 94, whilst the second connector 93 engages with and is connected to the second feedback transfer structure 95. The motor 90 is used to move the actuator 44 and beam 91 between the first and second positions depending on whether haptic feedback is desired to first surface 42 or the second surface 52. Thus, the controller can be configured to provide haptic feedback to one side or the other side (and thus to one hand or the other hand) using a single haptic actuator. In another embodiment, each of the first and second connectors are separately controllable (eg by separate beams connected to separate motors) so that haptic feedback can be provided to neither surfaces, the first surface only, the second surface only, or both the first and second surfaces.

The controllers may be constructed out of suitable material such as plastics to provide strength and durability while keeping the controller lightweight. The vibration is supplied using the same offset motors that are used within commercial Xbox controllers. The hardware (two hanged controller) maximises accessibility through both form and function. The design can accommodate different hand sizes (small hands through to large hands), and provides isolated haptic (or vibration) feedback to a selected hand, and encourages intuitive control.

A treatment system can be provided comprising the input apparatuses described above with a computer system comprising a display device, a processor and a memory. The memory can comprise instructions to cause the processor to execute an interactive computer game which provides haptic feedback to the patient, via the input apparatus, wherein the haptic feedback is isolated to one of the patient's hands. In another aspect, a computer readable medium (which may be non-transitory such as stored on an optical disk, hard disk or other medium) comprising instructions for causing a processor to execute an interactive computer game in which haptic feedback is generated to one of the first or second haptic actuators in an input apparatus as described above. The computer readable medium can further comprise instructions for executing functions described above, such as contextually relevant haptic feedback, high quality graphics and sounds, game play repeatability, logging and game configuration. This may further comprise instructions to configuration which haptic actuator to actuate for a given user (or patient). Thus, the game may require a user to logon or sign in to play. For non-patient players (or non-therapeutic play), the game can be configured to provide haptic feedback to both sides. Selection of which haptic actuator is to be actuated for a user can be secured or restricted, such as by requiring a password or other authentication token before a change can be made. This could be done locally or remotely, for example to allow a therapist to remotely configure the settings. The game may also comprise instructions for transmitting logging data to a remote computer or to a remote user such as a therapist to allow analysis of a patient's progress.

Other variations of the methods, apparatus and system described are also possible. In one embodiment the method of treatment and the controller can be used with existing games which produce haptic signals or output, but in which the controller selectively directs this generic haptic feedback to a previously selected hand. In one embodiment, the controller is preconfigured and locked into a haptic mode prior to connection of the controller to the computing device executing the game. That is, the computing device and the game software are unaware that selective haptic feedback is being delivered to the user (player). The controller could be locked into a haptic mode, in which the first haptic portion or second haptic portion is selected, and then all haptic feedback signals are directed to the selected haptic portion (until the controller is reconfigured). This could be performed using a separate configuration or interface application executed on the same or another computing device. This configuration utility may execute or run the administration module 1320 illustrated in FIG. 15. Alternatively, the configuration of the controller could be performed using a physical switch on the controller, or using the input button 12, for example by entering a series of inputs within a certain time. For example, a user could press and hold the input button for 10 seconds, and then push the controller to the desired side that haptic feedback is to be provided to. The control circuit 14 in the controller could interpret and store the selected haptic mode.

In another embodiment, a configuration application or interface could be provided to allow configuration of the controller when connected to a device, or interception of haptic feedback commands. That a user could connect the controller to a computing device, and the device would load appropriate drivers and load the configuration/interface application. A user could then execute this application and select the haptic mode, ie which side or haptic portion that any future haptic feedback is to be sent to. Alternatively, this selection could be automated based upon login credentials of the person currently logged into the computing device. The configuration application could store user profiles and simply lookup the haptic mode associated with the currently logged in user when the controller is connected to the computing device. This would avoid the need for launching the configuration utility once the controller is connected to the computing device or apparatus. The configuration utility can communicate and configure the controller based upon the desired haptic mode, or alternatively act as an interface between the game and/or computing device and the controller. In this latter case, it could receive haptic signals directed to the controller, and then send haptic feedback signals directed at the selected first or second haptic portion. Using the above embodiments, the controller could be connected and used as an input apparatus with a standard computing device, eg an IPAD or PC, and allow a user to play a standard game that includes haptic feedback (eg The Need For Speed).

Embodiments of the method of treatment using a serious game approach and an associated input apparatus have been described herein. Unlike most prior art serious game methods which attempt to mimic or provide physical therapy to target motor capabilities, the present embodiments have been designed to utilise an interactive haptic computer gaming system to influence sensory function of the patients. The method of therapy may be used to treat patients with sensory agnosia such as patients with Cerebral Palsy, or recovering from stroke or other injuries or illnesses. Without being limited by any specific theory it is thought that repeated therapy in which selective haptic feedback is provided to an affected hand (and by extension the limb) leads to neural recognition of the afferent nerve signals and subsequent neural reprogramming (ie neuroplasticity) to reinforce connections in the brain to nerves in the affected limb and thus improve touch sensitivity and train/retrain the impaired sense. Further, the treatment can be provided as a serious game which only requires minimal movement rather than the large scale gross range of movement used in physical therapy game. This is more similar to a conventional game and is thus more appealing to children (and many adults) than traditional therapies which leads to better compliance and patient outcomes.

The serious games have been specifically designed to be accessible and to maximise sensory interaction and appeal so as to provide both entertainment value and therapeutic value. They are visually engaging featuring high quality graphics, incorporate sounds wherever possible, and introduce the element of tactile sensory feedback (using the vibration capability), which enables the patient to 'feel' the game. This feedback increases the realism of the game by applying forces that are similar or representative to those that would be felt if actually performing the task. The haptic gaming system provides children with a unique way of coupling the playing of interactive and entertaining games that are cognitively engaging with meaningful, contextually relevant and appropriate tactile sensory cues at their hands. This is an important feature as it provides afferent tactile stimulation to the child during the game. Previous post stroke studies have indicated that the frequency of exposure to tactile vibrations must be high to re-train sensory function. Hence, the mode of delivery (using an 'in-home' setting) and methodology (using interactive computer games) has been chosen in order to maximise adherence and therefore success. A system comprising a suite of games provides choice, minimises game fatigue and/or boredom, and improves the likelihood that the child will use the system because they can find and play a game they like. The software (games) has been designed to be modular using procedural generation so that most of the games are unique when played, thereby increasing repeat gameplay. Being custom-made, the gaming system logs all aspects of gameplay (such as the amount of vibration received, the number of times a game was played, the joystick position and movement during game play, and all high scores), providing important information for assessing the level of engagement and the amount of vibration feedback each child received when played.

Other variations of the methods, apparatus and system described are also possible, and may be used in a range of applications. As previously stated, it is to be understood that the method is for treating sensory agnosia irrespective of the underlying cause (eg CP, stroke, trauma, etc), and may be used to treat patients of any age. Further, the controller may be used to treat other conditions or in other applications where selective provision of (isolated) haptic feedback is desirable or advantageous. For example, it could be used as part of a sensory test such as assessing nerve damage by selectively providing feedback to one hand or the other and asking the patient to report on the intensity, or by otherwise measuring the patient's response. Selection of the haptic portion or side to which haptic feedback is provided may be performed via a command sent to the controller (ie software control), by controlling the signal or signals sent to the controller (eg providing a power signal to the selected haptic actuator but not the other actuator), via a switch on the controller, or by using the input capabilities of the controller, eg one or more of sensing orientation, duration of button press, or order of button press and/or orientation changes.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number of source code or object code segments or instructions, and may reside in any computer readable medium such as a RAM memory, flash memory, ROM memory, EPROM memory, registers, hard disk, a removable disk, a CD-ROM, a DVD-ROM or any other form of computer readable medium. In the alternative, the computer readable medium may be integral to the processor. The processor and the computer readable medium may reside in an ASIC or related device. The software codes may be stored in a memory unit and executed by a processor. The memory unit may be implemented within the processor or external to the processor, in which case it can be communicatively coupled to the processor via various means as is known in the art. The controller can be connected to static computing device such as a desktop computing device or gaming system, a mobile device including laptops, tablets, smart phone, or a specialised computing device integrated into an assisted technology device such as a wheelchair.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims. Please note that the following claims are not intended to limit the scope of what may be claimed in any future patent applications based on the present application. Integers may be added to or omitted from the claims at a later date so as to further define or re-define the invention.

The invention claimed is:

1. A method for treating a patient, the method comprising:
providing a two-handed controller operable within the patient's known motor capabilities;
enabling the patient to engage in an interactive computer game using the two-handed controller;
detecting when both hands of the patient are in contact with the controller, and only allowing the patient to interact with the game when both hands are detected as being in contact with the controller; and
providing haptic feedback to the patient via the two handed game controller as the patient engages with the interactive computer game, wherein the haptic feedback is isolated to one of the patient's hands.

2. The method as claimed in claim 1 wherein the two-handed controller comprises a first haptic portion for providing haptic feedback to a first hand, and a second haptic portion for providing haptic feedback to a second hand, and the first haptic portion is isolated from the second haptic portion, and providing haptic feedback to the patient comprises selecting the first haptic portion or the second haptic portion and providing haptic feedback to the selected haptic portion.

3. The method as claimed in claim 2, further comprising locating the first and second haptic portions in locations to maximise delivery of haptic feedback to the patients fingers and palms.

4. The method as claimed in claim 2, wherein the first haptic portion is a first side of the two handed controller and the second haptic portion is a second side of the two handed controller.

5. The method as claimed in claim 1, wherein the two handed game controller provides movement in two axes.

6. The method as claimed in claim 5, wherein the two handed controller is a pivoting controller and the patient engages in the interactive computing game solely by pivoting the controller using two hands.

7. The method as claimed in claim 1, wherein the interactive computer game provides a range of contextually relevant haptic feedback of varying durations and intensities.

8. The method as claimed in claim 7, further comprising the step of logging the haptic feedback provided to a patient engaging in the interactive computer game wherein events in the interactive computer game are assigned a relative feedback strength normalised to a reference feedback intensity and duration s and logging the haptic feedback comprises logging the duration and strength of each haptic feedback event.

9. The method as claimed in claim 7, further comprising logging one or more usage metrics of the patient engaging in the interactive computer game, wherein the one or more usage metrics are selected from the group comprising time, day, duration of session, and controller position.

10. The method as claimed in claim 1, wherein the step of enabling the patient to engage in an interactive computer game further comprises providing at least one interactive computer game comprising one or more levels, and the one or more levels comprise procedurally generated content to provide repeated game play.

11. The method as claimed in claim 1, wherein the patient is diagnosed with Cerebral Palsy.

12. An input apparatus comprising:
a base;
a top section;
a mount for mounting the top section relative to the base, wherein the mount allows the top section to move in two axes relative to the base to define the input provided by the device;
a communications interface;
a first surface on a first side of the top section, for a first hand of a user;
a second surface on a second side of the top section, for a second hand of the user; and
at least one haptic actuator to provide haptic feedback to the first surface or the second surface,
a first proximity detector for detecting if a hand is placed on the first surface,
a second proximity detector for detecting if a hand is placed on the second surface,
wherein the first surface and the second surface are substantially isolated such that the haptic feedback can be provided independently to the first or second surface, and the input apparatus is configured so that haptic feedback is only provided if the first proximity detector detects a hand is placed on the first surface and the second proximity detector detects a hand is placed on the second surface, and an interrupt signal is sent via the communications interface if one or both of the first and second proximity detectors detects that a hand is not placed on the respective first or second surface.

13. The input apparatus as claimed in claim 12, further comprising a controller for receiving a haptic selection command via the communications interface and enabling haptic feedback to be provided to the first surface or the second surface based upon the haptic selection command.

14. The input apparatus as claimed in claim 13, wherein the at least one haptic actuator comprises a first haptic actuator to provide haptic feedback to the first surface, and a second haptic actuator to provide haptic feedback to the second surface, and the first surface is isolated from the second surface.

15. The input apparatus as claimed in claim 14, wherein the first haptic actuator is mounted in a haptic module mount located in the first side and the first side is mounted to a central plate via a plurality of isolation mounts, and the second haptic actuator is mounted in a haptic module mount located in the second side and the second side is mounted to the central plate via a plurality of isolation mounts.

16. The input apparatus as claimed in claim 12, further comprising at least one strap for strapping a hand to either the first or the second surface.

17. The input apparatus as claimed in claim 12, wherein the first surface and the second surface are located to maximise delivery of haptic feedback to the patient's fingers and palms.

18. The input apparatus as claimed in claim 12, wherein the first and second sides are concave and are arranged relative to each other such that in use a user is required to contact both the first and second surfaces to pivot the controller.

19. A treatment system comprising:
   an input apparatus comprising:
      a base;
      a top section;
      a mount for mounting the top section relative to the base, wherein the mount allows the top section to move in two axes relative to the base to define the input provided by the device;
      a communications interface;
      a first surface on a first side of the top section, for a first hand of a user;
      a second surface on a second side of the top section, for a second hand of the user; and
      at least one haptic actuator to provide haptic feedback to the first surface or the second surface,
      a first proximity detector for detecting if a hand is placed on the first surface,
      a second proximity detector for detecting if a hand is placed on the second surface,
   wherein the first surface and the second surface are substantially isolated such that the haptic feedback can be provided independently to the first or second surface, and the input apparatus is configured so that haptic feedback is only provided if the first proximity detector detects a hand is placed on the first surface and the second proximity detector detects a hand is placed on the second surface, and an interrupt signal is sent via the communications interface if one or both of the first and second proximity detectors detects that a hand is not placed on the respective first or second surface;
   a display device;
   a processor; and
   a memory, wherein the memory comprises instructions to cause the processor to execute an interactive computer game wherein the interactive computer game provides haptic feedback to the patient from the computer game via the input apparatus, and the haptic feedback is isolated to one of the first surface or the second surface, and the system is configured to detect if both hands of the patient are respectively in contact with the first and second surface of the input apparatus using the interrupt signal and only allow game play if both hands are detected as being in contact with the first and second surface.

20. The treatment system as claimed in claim 19, wherein the instructions provide a range of contextually relevant haptic feedback of varying durations and intensities.

21. The treatment system as claimed in claim 20, wherein the memory further comprises instructions for logging the haptic feedback provided to the input apparatus whilst executing the interactive computer game wherein events in the interactive computer game are assigned a relative feedback strength normalised to a reference feedback intensity and duration s and logging the haptic feedback comprises logging the duration and strength of each haptic feedback event.

22. The treatment system as claimed in claim 20, wherein the memory further comprises instructions for logging one or more usage metrics of a patient engaging in the interactive computer game, wherein the one or more usage metrics are selected from the group comprising time, day, duration of session, and input apparatus position.

23. The treatment system as claimed in claim 19, wherein the interactive computer game comprises one or more levels, and the one or more levels comprise procedurally generated content to provide repeated game play.

\* \* \* \* \*